(12) United States Patent
Kadereit et al.

(10) Patent No.: US 8,846,691 B2
(45) Date of Patent: Sep. 30, 2014

(54) HETEROCYCLIC CARBOXYLIC ACID DERIVATIVES HAVING A 2,5,7-SUBSTITUTED OXAZOLOPYRIMIDINE RING

(75) Inventors: Dieter Kadereit, Frankfurt am Main (DE); Matthias Schaefer, Frankfurt am Main (DE); Stephanie Hachtel, Frankfurt am Main (DE); Axel Dietrich, Frankfurt am Main (DE); Thomas Huebschle, Frankfurt am Main (DE); Andreas Gille, Frankfurt am Main (DE); Katrin Hiss, Frankfurt am Main (DE)

(73) Assignee: Sanofi, Paris (FR)

( * ) Notice: Subject to any disclaimer, the term of this patent is extended or adjusted under 35 U.S.C. 154(b) by 248 days.

(21) Appl. No.: 13/521,829

(22) PCT Filed: Jan. 12, 2011

(86) PCT No.: PCT/EP2011/050299
§ 371 (c)(1),
(2), (4) Date: Dec. 7, 2012

(87) PCT Pub. No.: WO2011/086078
PCT Pub. Date: Jul. 21, 2011

(65) Prior Publication Data
US 2013/0158051 A1 Jun. 20, 2013

(30) Foreign Application Priority Data

Jan. 13, 2010 (EP) .................................. 10305037

(51) Int. Cl.
*A01N 43/90* (2006.01)
*A61K 31/519* (2006.01)
*C07D 239/00* (2006.01)
*C07D 498/04* (2006.01)

(52) U.S. Cl.
CPC .................................. *C07D 498/04* (2013.01)
USPC ........................................ 514/260.1; 544/255

(58) Field of Classification Search
None
See application file for complete search history.

*Primary Examiner* — Jeffrey H Murray

(57) ABSTRACT

The invention relates to oxazolopyrimidine compounds of formula (I), where A, $R^1$, $R^2$, $R^3$, $R^4$, X and Y are defined as stated in the claims. The compounds of formula I are suitable, for example, for wound healing.

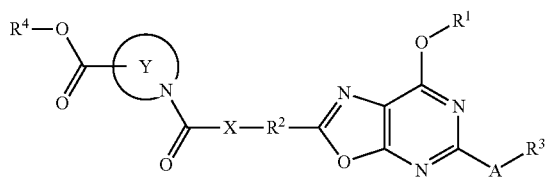

(I)

16 Claims, No Drawings

HETEROCYCLIC CARBOXYLIC ACID DERIVATIVES HAVING A 2,5,7-SUBSTITUTED OXAZOLOPYRIMIDINE RING

The present invention relates to heterocyclic carboxylic acid derivatives having a 2,5,7-substituted oxazolopyrimidine ring, and to their physiologically acceptable salts.

Structurally similar compounds are already described in the prior art (see WO 2009/154775), which are suitable for treating multiple sclerosis. The mode of action of these compounds consists in causing a desensitization of the EDG 1 signal pathway by activating the EDG 1 receptor (so-called superagonism), which is then equivalent to a functional antagonism of the EDG 1 signal pathway. Systemically means that especially on lymphocytes, the EDG 1 signal pathway is permanently suppressed, as a result of which these cells can no longer chemotactically follow the S1P gradient between blood and lymph fluid. This means that the affected lymphocytes can no longer leave the secondary lymphatic tissue (increased homing) and the number of freely circulating lymphocytes in the plasma is greatly reduced. This deficiency of lymphocytes in the plasma (lymphopenia) brings about immunosuppression which is obligatorily required for the mechanism of action of the EDG 1 receptor modulators described in WO 2009/154775.

The object of the present invention was to provide compounds which are suitable specifically for wound healing and in particular for the treatment of wound healing disorders in patients with diabetes. In addition, it was desirable to provide compounds which are suitable for the treatment of diabetic foot syndrome (DFS). Furthermore, it was desirable to achieve a reproducible activation of the EDG 1 receptor signal pathway which thereby permits, in pharmacological terms, a persistent activation of the EDG 1 signal pathway.

The present invention relates to oxazolopyrimidine compounds of the formula I.

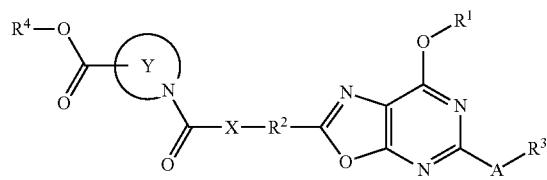

I in which A, $R^1$, $R^2$, $R^3$, $R^4$, X and Y are as defined below. The mechanism of action of the compounds of the formula I is thus not based on desensitization of the EDG 1 signal pathway and is therefore in diametral opposition to the mechanism of action described in WO 2009/154775. The invention furthermore relates to processes for the preparation of compounds of the formula I, their use, in particular as active ingredients in pharmaceuticals, and pharmaceutical compositions comprising them.

Compared with healthy people, patients with diabetes have delayed wound healing and an increased rate of infection, especially in the case of long-term hyperglycemia, caused for example by poor blood sugar regulation. The causes include circulation disorders, especially in the area of the small vessels, which lead to impaired oxygen and nutrient supply of the tissue. Moreover, the cell division and cell migration rate of keratinocytes, fibroblasts and dermal endothelial cells is reduced. Additionally, the activity of various defense cells (granulocytes) with reduced phagocytosis (engulfing and destruction of bacteria) is restricted. The action of antibodies (immunoglobulins) against bacteria at high blood sugar levels is also restricted. Accordingly, wounds and infections in patients with diabetes have to be cared for in a particular way.

The Edg 1 receptor is a member of the endothelial differentiation gene (Edg) receptor family of currently eight identified class A GPCRs (G-protein coupled receptors). This family can be divided into subfamilies of sphingosine-1-phosphate (SIP)-activated receptors (five members) and receptors activated by lysophosphatidic acid (LPA; three members). The endogenous ligand S1P is a pluripotent lysophospholipid acting on different cell types by activating GPCRs from the Edg receptor family, namely Edg 1 (=S1P1), Edg 3 (=S1P3), Edg 5 (=S1P2), Edg 6 (=S1P4) and Edg 8 (S1P5). Although S1P is also described as an intracellular messenger, numerous cellular responses of S1P are mediated via the activation of Edg receptors. S1P is generated by the enzyme family of sphingosine kinases (SPHK) and degraded by different phosphatases or lyases.

The present invention provides oxazolopyrimidine compounds of the formula I in any of their stereoisomeric forms, or a mixture of stereoisomeric forms in any ratio, or a physiologically acceptable salt thereof, or a physiologically acceptable solvate of such a compound or such a salt,

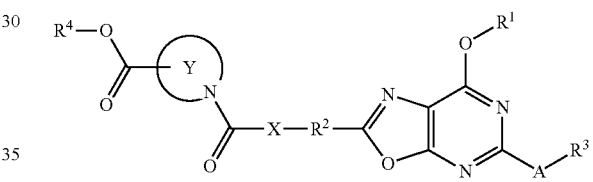

I wherein
A is selected from the group consisting of NH, O and S;
X is selected from the group consisting of $(C_1$-$C_6)$-alkanediyl, $(C_2$-$C_6)$-alkenediyl, $(C_2$-$C_6)$-alkynediyl, $(C_3$-$C_7)$-cycloalkanediyl and $(C_1$-$C_6)$-alkanediyloxy, all of which are optionally substituted by one or more identical or different substituents selected from the group consisting of fluorine and hydroxyl, where the oxygen atom of the $(C_1$-$C_6)$-alkanediyloxy group is attached to the group $R^2$;
Y is a 4-membered to 7-membered saturated or partially unsaturated monocyclic or bicyclic heterocycle which, in addition to the ring nitrogen atom shown in formula I, contains 0, 1, 2 or 3 identical or different ring heteroatoms selected from the group consisting of N, O and S, where one or two of the additional ring nitrogen atoms may carry a hydrogen atom or a $(C_1$-$C_4)$-alkyl substituent and one of the ring sulfur atoms may carry one or two oxo groups and where the heterocycle is optionally substituted at one or more ring nitrogen atoms by identical or different $(C_1$-$C_4)$-alkyl substituents;
$R^1$ is selected from the group consisting of $(C_1$-$C_6)$-alkyl, $(C_2$-$C_6)$-alkenyl, $(C_2$-$C_6)$-alkynyl, $(C_3$-$C_7)$-cycloalkyl-$C_tH_{2t}$— and Het-$C_tH_{2t}$—, in which t is selected from the group consisting of 0, 1, 2 and 3;
$R^2$ is selected from the group consisting of phenylene and a bivalent radical of an aromatic 5-membered or 6-membered monocyclic heterocycle which contains 1, 2 or 3 identical or different ring heteroatoms selected from the group consisting of N, O and S, where one of the ring nitrogen atoms may carry a hydrogen atom or a substituent $R^{21}$ and where the phenylene and the bivalent radical of an aromatic heterocycle are optionally substituted at one or more ring carbon atoms by identical or different substituents $R^{22}$;

$R^3$ is selected from the group consisting of $(C_1-C_6)$-alkyl, $(C_2-C_6)$-alkenyl, $(C_2-C_6)$-alkynyl, $(C_3-C_7)$-cycloalkyl-$C_uH_{2u}$— and Het-$C_vH_{2v}$—, in which u and v are selected from the group consisting of 1 and 2, or $R^3$ is a radical of a saturated or unsaturated 3-membered to 10-membered monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups and where the radical of a ring is optionally substituted at one or more ring carbon atoms by identical or different substituents $R^{31}$, with the proviso that $R^3$ may not represent $(C_1-C_6)$-alkyl if A represents S;

$R^4$ is selected from the group consisting of hydrogen, $(C_1-C_4)$-alkyl and $(C_3-C_7)$-cycloalkyl-$C_zH_{2z}$—, where z is selected from the group consisting of 0, 1 and 2;

$R^{21}$ is selected from the group consisting of $(C_1-C_4)$-alkyl and $(C_3-C_7)$-cycloalkyl-$C_wH_{2w}$— and oxy, where w is selected from the group consisting of 0, 1 and 2;

$R^{22}$ is selected from the group consisting of halogen, hydroxyl, $(C_1-C_4)$-alkyl-, $(C_1-C_4)$-alkyloxy, $(C_1-C_4)$-alkyl-S(O)$_m$—, amino, nitro, cyano, hydroxycarbonyl, $(C_1-C_4)$-alkyloxycarbonyl, aminocarbonyl and aminosulfonyl;

$R^{31}$ is selected from the group consisting of halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di(($C_1-C_4$)-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di(($C_1-C_4$)-alkyl)aminosulfonyl;

Het is a radical of a saturated 4-membered to 7-membered monocyclic heterocycle which contains 1 or 2 identical or different ring heteroatoms selected from the group consisting of N, O and S and which is attached via a ring carbon atom, where the radical of a heterocycle is optionally substituted by one or more identical or different substituents selected from the group consisting of fluorine and $(C_1-C_4)$-alkyl;

m is selected from the group consisting of 0, 1 and 2, where all numbers m are independent of one another;

where all cycloalkyl and cycloalkanediyl groups independently of one another and independently of other substituents are optionally substituted by one or more identical or different substituents selected from the group consisting of fluorine and $(C_1-C_4)$-alkyl;

where all alkyl, alkanediyl, $C_tH_{2t}$, $C_uH_{2u}$, $C_vH_{2v}$, $C_wH_{2w}$, $C_zH_{2z}$, alkenyl, alkenediyl, alkynyl and alkynediyl groups independently of one another and independently of other substituents are optionally substituted by one or more fluorine substituents.

Structural elements such as groups, substituents, heteroring members, numbers or other features, for example alkyl groups, groups like $R^{22}$ or $R^{31}$, numbers like m, u and v, which can occur several times in the compounds of the formula I, can all independently of one another have any of the indicated meanings and can in each case be identical to or different from one another. For example, the alkyl groups in a dialkylamino group can be identical or different.

Alkyl, alkenyl and alkynyl groups can be linear, i.e. straight-chain, or branched. This also applies when they are part of other groups, for example alkyloxy groups (=alkoxy groups, alkyl O groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n pentyl, 1-methylbutyl, isopentyl, neopentyl and tert-pentyl, and hexyl including n-hexyl, 3,3-dimethylbutyl and isohexyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

Insofar as applicable, the above explanations of the alkyl, alkenyl and alkynyl groups correspond to bivalent alkyl groups such as the groups alkanediyl, $C_tH_{2t}$, $C_uH_{2u}$, $C_vH_{2v}$, $C_wH_{2w}$, and $C_zH_{2z}$ and divalent alkenyl groups and alkynyl groups like the groups alkenediyl and alkynediyl, which can thus likewise be straight-chain or branched. The double bonds and triple bonds in alkenediyl and alkynediyl groups can be located in any positions. In one embodiment of the invention, alkenediyl groups contain one double bond and alkynediyl groups contain one triple bond. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—, examples of divalent alkenyl groups are —CH=CH—, —CH$_2$—CH=CH—, —CH=CH—CH$_2$—, —CH=CH—CH—CH$_2$—, —CH$_2$—CH$_2$—CH=CH—, —C(CH$_3$)=C(CH$_3$)— and examples of divalent alkynyl groups are —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—. If a number in a divalent group such as the number t in the group $C_tH_{2t}$, for example, is 0 (=zero), the two groups which are attached to the contemplated group, such as $C_tH_{2t}$, are directly connected to one another via a single bond.

The number of ring carbon atoms in a cycloalkyl group can be 3, 4, 5, 6 or 7. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 6. This applies accordingly to divalent cycloalkyl groups, i.e. cycloalkanediyl groups, which can be bonded to the adjacent groups via one or two ring carbon atoms. Examples of cycloalkyl groups are cyclopropyl, cyclobutyl, cyclopentyl, cyclohexyl and cycloheptyl. Examples of divalent cycloalkyl groups are cyclopropane-1,1-diyl, cyclopropane-1,2-diyl, cyclobutane-1,3-diyl, cyclopentane-1,1-diyl, cyclopentane- 1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,4-diyl.

Independently of one another and independently of any other substituents, cycloalkyl and cycloalkanediyl groups are optionally substituted by one or more identical or different $(C_1-C_4)$-alkyl substituents which can be located in any positions, i.e., cycloalkyl groups can be unsubstituted by alkyl substituents or substituted by alkyl substituents, for example by 1, 2, 3 or 4, or by 1 or 2, $(C_1-C_4)$-alkyl substituents, for example by methyl groups. Examples of alkyl-substituted cycloalkyl and cycloalkanediyl groups are 4-methylcyclohexyl, 4-tert-butylcyclohexyl or 2,3-dimethylcyclopentyl, 2,2-dimethylcyclopropane-1,1-diyl, 2,2-dimethylcyclopropane-1,2-diyl, 2,2-dimethylcyclopentane-1,3-diyl, 6,6-dimethylcycloheptane-1,4-diyl. Examples of cycloalkylalkyl groups, which can represent groups such as $(C_3-C_7)$-cycloalkyl-$C_rH_{2r}$—, for example, are cyclopropylmethyl, cyclobutylmethyl, cyclopentylmethyl, cyclohexylmethyl, cycloheptylmethyl, 1-cyclopropylethyl, 2-cyclopropylethyl, 1-cyclobutylethyl, 2-cyclobutylethyl, 2-cyclopentylethyl, 2-cyclohexylethyl, 2-cycloheptylethyl.

Independently of one another and independently of any other substituents, alkyl groups, divalent alkyl groups, alkenyl groups, divalent alkenyl groups, alkynyl groups, divalent alkynyl groups, cycloalkyl groups and divalent cycloalkyl groups are optionally substituted by one or more fluorine substituents which can be located in any positions, i.e., said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of such fluorine-substituted groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl, 2,2-difluorocyclopropane-1,2-diyl. Examples of alkyloxy groups in which the alkyl moiety is fluorine-substituted are trifluoromethoxy, 2,2,2-trifluoroethoxy, pentafluoroethoxy and 3,3,3-trifluoropropoxy. In one embodiment of the invention, the total number of fluorine substituents and $(C_1-C_4)$-alkyl substituents, which independently of any other substituents are optionally present on cycloalkyl and cycloalkanediyl groups in the compounds of the formula I, is 1, 2, 3, 4, 5, 6, 7, 8, 9, 10 or 11, in another embodiment 1, 2, 3, 4, 5, 6, 7, 8 or 9, in another embodiment 1, 2, 3, 4 or 5, in another embodiment 1, 2, 3 or 4.

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. In one embodiment of the invention the total number of nitro substituents in a compound of the formula I is not greater than two. Aromatic nitrogen heterocycles which in the parent ring system carry a hydrogen atom on a ring nitrogen atom in a 5-membered ring, such as a pyrrole, imidazole, indole or benzimidazole ring, for example, can be substituted on the carbon atoms and/or on such ring nitrogen atoms. In one embodiment of the invention, substituents on such ring nitrogen atoms are selected from $(C_1-C_4)$-alkyl groups, i.e. such ring nitrogen atoms in aromatic heterocycles carry a hydrogen atom or a $(C_1-C_4)$-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent, or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzimidazole, for example, and in a non-aromatic ring in which they are bridgehead atoms or are part of a double bond, and they occur as ring nitrogen atoms via which a ring is bonded. Suitable ring nitrogen atoms in aromatic heterocycles in the compounds of the formula I, such as the ring nitrogen atom in a pyridine ring, specifically a ring nitrogen atom in an aromatic heterocycle representing $R^2$, can also carry an oxy substituent $O^-$ and be present as an N-oxide, and such ring nitrogen atoms can also be present as quaternary salt, for example as N—$(C_1$-$C_4)$-alkyl salt such as N-methyl salt, wherein in one embodiment of the invention the counter anion in such a quaternary salt is a physiologically acceptable anion which is derived from an acid that forms a physiologically acceptable salt. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring. This statement relating to the monovalent residues applies accordingly to the respective divalent residues, such as phenylene groups representing $R^2$, for example, which thus can likewise be unsubstituted or substituted, for example by 1, 2, 3 or 4, or by 1, 2 or 3, or by 1 or 2, or by 1, identical or different substituents which can be located in any positions.

In radicals of aromatic heterocycles representing $R^2$ or $R^3$, which may be designated as heteroaryl and heteroarylene groups, as well as in all other heterocyclic rings in the compounds of the formula I including the group Het and the non-aromatic heterocyclic groups representing $R^3$, the ring heteroatoms are generally selected from the group consisting of N, O and S, where N includes ring nitrogen atoms which carry a hydrogen atom or a substituent as well as ring nitrogen atoms which do not carry a hydrogen atom or a substituent. Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms selected from the group consisting of oxygen and sulfur cannot be present in adjacent ring positions of any heterocycle. Saturated rings do not contain a double bond within the ring. Unsaturated ring systems can be aromatic or partially unsaturated including partially aromatic, in which latter case one ring in a bicyclic ring system is aromatic and the ring system is bonded via an atom in the non-aromatic ring. Depending on the respective group, unsaturated rings can contain one, two, three, four or five double bonds within the ring. Aromatic groups contain a cyclic system of six or ten delocalized pi electrons in the ring. Depending on the respective group, saturated and non-aromatic unsaturated heterocyclic rings, including Het and non-aromatic groups representing $R^3$, can be 3-membered, 4-membered, 5-membered, 6-membered, 7-membered, 8-membered, 9-membered or 10-membered. In one embodiment of the invention, aromatic heterocyclic rings are 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings, wherein the 8-membered, 9-membered or 10-membered bicyclic rings are composed of two fused 5-membered rings, a 5-membered ring and a 6-membered ring which are fused to one another, and two fused 6-membered rings, respectively. In bicyclic aromatic heterocyclic groups, one or both rings can contain heteroring members, and one or both rings can be aromatic. In general, bicyclic ring systems containing an aromatic ring and a non-aromatic ring are regarded as aromatic when they are bonded via a carbon atom in the aromatic ring, and as non-aromatic when they are bonded via a carbon atom in the non-aromatic ring. Unless stated otherwise, heterocyclic groups including aromatic heterocyclic groups can be bonded via any suitable ring carbon atom and, in the case of nitrogen heterocycles, via any suitable ring nitrogen atom. In one embodiment of the invention, an aromatic heterocyclic group in a compound of the formula I, independently of any other aromatic heterocyclic group, is bonded via a ring carbon atom, in another embodiment via a ring nitrogen atom. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 1, wherein the ring heteroatoms can be identical or different. Heterocyclic groups which are optionally substituted, can independently of any other heterocyclic group be unsubstituted or substituted by one or more identical or different substituents, for example by 1, 2, 3, 4 or 5, or by 1, 2, 3 or 4, or by 1, 2 or 3, or by 1 or 2, or by 1 substituents, which are indicated in the definition of the respective group. Substituents on heterocyclic groups can be located in any positions. For example, in a pyridin-2-yl group substituents can be located in the 3-position and/or 4-position and/or 5-position and/or 6-position, in a pyridin-3-yl group substituents can be located in the 2-position and/or 4-position and/or 5-position and/or 6-position, in a pyridin-4-yl group substituents can be located in the 2-position and/or 3-position and/or 5-position and/or 6-position.

Examples of parent heterocycles, from which heterocyclic groups including aromatic heterocyclic groups, saturated heterocyclic groups and non-aromatic unsaturated heterocyclic groups can be derived, are azete, oxete, pyrrole, furan, thiophene, imidazole, pyrazole, [1,3]dioxole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4] thiadiazole, [1,3,4]thiadiazole, tetrazole, pyridine, pyran, thiopyran, pyridazine, pyrimidine, pyrazine, [1,3]oxazine, [1,4]oxazine, [1,3]thiazine, [1,4]thiazine, [1,2,3]triazine, [1,3]dithiine, [1,4]dithiine, [1,2,4]triazine, [1,3,5]triazine, [1,2,4,5]tetrazine, azepine, [1,3]diazepine, [1,4]diazepine, [1,3]oxazepine, [1,4]oxazepine, [1,3]thiazepine, [1,4]thiazepine, azocine, azecine, cyclopenta[b]pyrrole, 2-azabicyclo[3.1.0]hexane, 3-azabicyclo[3.1.0]hexane, 2-oxa-5-azabicyclo[2.2.1]heptane, indole, isoindole, benzothiophene, benzofuran, [1,3]benzodioxole (=1,2-methylenedioxybenzene), [1,3]benzoxazole, [1,3]benzothiazole, benzoimidazole, thieno[3,2-c]pyridine, chromene, isochromene, [1,4]benzodioxine, [1,4]benzoxazine, [1,4]benzothiazine, quinoline, isoquinoline, cinnoline, quinazoline, quinoxaline, phthalazine, thienothiophene, [1,8]naphthyridine and other naphthyridines, pteridine, and the respective saturated and partially saturated heterocycles in which one or more, for example one, two, three, four or all double bonds within the ring system including double bonds in aromatic ring are replaced with single bonds, such as azetidine, oxetane, pyrrolidine, tetrahydrofuran, tetrahydrothiophene, imidazolidine, oxazolidine, thiazolidine, dihydropyridine, piperidine, tetrahydropyran, piperazine, morpholine, thiomorpholine, azepane, chroman, isochroman, [1,4]benzodioxane (=1,2-ethylenedioxybenzene), 2,3-dihydrobenzofuran, 1,2,3,4-tetrahydroquinoline, 1,2,3,4-tetrahydroisoquinoline, for example.

Examples of residues of aromatic heterocycles, which can occur in the compounds of the formula I, are thiophenyl (=thienyl) including thiophen-2-yl and thiophen-3-yl, pyridinyl (=pyridyl) including pyridin-2-yl (=2-pyridyl), pyridin-3-yl (=3-pyridyl) and pyridin-4-yl (=4-pyridyl), imidazolyl including, for example, 1H-imidazol-1-yl, 1H-imidazol-2-yl, 1H-imidazol-4-yl and 1H-imidazol-5-yl, [1,2,4]triazolyl including 1H-[1,2,4]-triazol-1-yl and 4H-[1,2,4-triazol-3-yl, tetrazolyl including 1H-tetrazol-1-yl and 1H-tetrazol-5-yl, quinolinyl (=quinolyl) including quinolin-2-yl, quinolin-3-yl, quinolin-4-yl, quinolin-5-yl, quinolin-6-yl, quinolin-7-yl and quinolin-8-yl, which all are optionally substituted as indicated in the definition of the respective group. Examples of residues of saturated and partially unsaturated heterocycles, which can occur in the compounds of the formula I, are azetidinyl, pyrrolidinyl including pyrrolidin-1-yl, pyrrolidin-2-yl and pyrrolidin-3-yl, 2,5-dihydro-1H-pyrrolyl, piperidinyl including piperidin-1-yl, piperidin-2-yl, piperidin-3-yl and piperidin-4-yl, 1,2,3,4-tetrahydropyridinyl, 1,2,5,6-tetrahydropyridinyl, 1,2-dihydropyridinyl, azepanyl, azocanyl, azecanyl, octahydrocyclopenta[b]pyrrolyl, 2,3-dihydrobenzofuranyl including 2,3-dihydrobenzofuran-7-yl, 2,3-dihydro-1H-indolyl, octahydro-1H-indolyl, 2,3-dihydro-1H-isoindolyl, octahydro-1H-isoindolyl, 1,2-dihydroquinolinyl, 1,2,3,4-tetrahydroquinolinyl, decahydroquinolinyl, 1,2-dihydroisoquinolinyl, 1,2,3,4-tetrahydroisoquinolinyl, 1,2,3,4-tetrahydroisoquinolinyl, decahydroisoquinolinyl, decahydroisoquinolinyl, 4,5,6,7-tetrahydrothieno[3,2-c]pyridinyl, pyrazolidinyl, imidazolidinyl, hexahydropyrimidinyl, 1,2-dihydropyrimidinyl, piperazinyl, [1,3]diazepanyl, [1,4]diazepanyl, oxazolidinyl, [1,3]oxazinanyl, [1,3]oxazepanyl, morpholinyl including morpholin-2-yl, morpholin-3-yl and morpholin-4-yl, [1,4]oxazepanyl, thiazolidinyl, [1,3]thiazinanyl, thiomorpholinyl including thiomorpholin-2-yl, thiomorpholin-3-yl and thiomorpholin-4-yl, 3,4-dihydro-2H-[1,4]thiazinyl, [1,3]thiazepanyl, [1,4]thiazepanyl, [1,4]thiazepanyl, oxetanyl, tetrahydrofuranyl, tetrahydrothienyl, isoxazolidinyl, isothiazolidinyl, oxazolidinyl, [1,2,4]-oxadiazolidinyl, [1,2,4]-thiadiazolidinyl, [1,2,4]triazolidinyl, [1,3,4]oxadiazolidinyl, [1,3,4]thiadiazolidinyl,

[1,3,4]triazolidinyl, 2,3-dihydrofuranyl, 2,5-dihydrofuranyl, 2,3-dihydrothienyl, 2,5-dihydrothienyl, 2,3-dihydropyrrolyl, 2,3-dihydroisoxazolyl, 4,5-dihydroisoxazolyl, 2,5-dihydroisoxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, tetrahydropyridazinyl, tetrahydropyrimidinyl, tetrahydropyrazinyl, tetrahydro[1,3,5]triazinyl, [1,3]dithianyl, tetrahydropyranyl, tetrahydrothiopyranyl, [1,3]dioxolanyl, 3,4,5,6-tetrahydropyridinyl, 4H-[1,3]thiazinyl, 1,1-dioxo-2,3,4,5-tetrahydrothienyl, 2-azabicyclo[3.1.0]hexyl including 2-azabicyclo[3.1.0]hex-2-yl, 3-azabicyclo[3.1.0]hexyl including 3-azabicyclo[3.1.0]hex-3-yl, 2-oxa-5-azabicyclo[2.2.1]-heptyl including 2-oxa-5-azabicyclo[2.2.1]-hept-5-yl, which all are bonded via any suitable ring carbon atom or ring nitrogen atom and are optionally substituted as indicated in the definition of the respective group.

Halogen is fluorine, chlorine, bromine or iodine. In one embodiment of the invention, any halogen in a compound of the formula I is independently of any other halogen selected from the group consisting of fluorine, chlorine and bromine, in another embodiment from fluorine and chlorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a C(O) (=C(=O)) group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S oxide group) in case it carries one oxo group, or it is an $S(O)_2$ group (=sulfone group, S,S dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts. Thus, the compounds of the formula I which contain an acidic group, such as a hydroxycarbonyl group (=carboxyl group =C(O)—OH group), can be present on such groups, and can be used according to the invention, as alkaline metal salts, alkaline earth metal salts or as ammonium salts, for example. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formula I which contain a basic group, i.e. a group which can be protonated such as an amino group or a nitrogen heterocycle, can be present on such groups, and can be used according to the invention, in the form of their addition salts with inorganic and organic acids. Examples for suitable acids include hydrogen chloride, hydrogen bromide, phosphoric acid, sulfuric acid, methanesulfonic acid, oxalic acid, acetic acid, trifluoroacetic acid, tartaric acid, lactic acid, benzoic acid, malonic acid, fumaric acid, maleic acid, citric acid, and other acids known to the person skilled in the art. If a compound of the formula I simultaneously contains an acidic group and a basic group in the molecule, the compound also includes, in addition to the salt forms mentioned, inner salts (=betaines, zwitterions). The salts of the compounds of the formula I can be obtained by customary methods which are known to the person skilled in the art like, for example, by contacting the compound of the formula I with an organic or inorganic acid or base in a solvent or diluent, or by anion exchange or cation exchange from another salt. The invention also includes all salts of the compounds of the formula I which, owing to low physiological compatibility of the salt-forming acid or base, are not directly suitable for use in pharmaceuticals but which can be used, for example, as intermediates for chemical reactions or for the preparation of physiologically acceptable salts.

The present invention includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

In one embodiment of the invention, A is selected from the group consisting of NH and O, in another embodiment of the invention, A is selected from the group consisting of NH and S, in another embodiment of the invention, A is selected from the group consisting of O and S, in another embodiment of the invention, A is NH, in another embodiment of the invention, A is O, in another embodiment of the invention, A is S.

The alkanediyl, alkenediyl and alkynediyl groups occurring in the group X can be linear or branched, as already indicated with respect to such groups in general, and these groups as well as cycloalkanediyl groups representing X can be bonded to the adjacent groups, i.e. to the heterocycle Y and to the group $R^2$ or, in the case of the group alkanediyloxy, to the oxygen atom of the alkanediyloxy group, via any positions. The adjacent groups can be bonded to the same carbon atom or to different carbon atoms in the group X. In one embodiment, the chain of carbon atoms in alkanediyl, alkenediyl and alkynediyl groups occurring in the group X which directly connects the heterocycle Y to the group $R^2$ or, in the case of the group alkanediyloxy, to the oxygen atom of the alkanediyloxy group, consists of 1, 2, 3 or 4 carbon atoms, in another embodiment of 1, 2 or 3 carbon atoms, in another embodiment of 1 or 2 carbon atoms, in another embodiment of 1 carbon atom. In the case of a cycloalkanediyl group representing X, in one embodiment the heterocycle Y and the group $R^2$ are bonded to two ring carbon atoms which are in 1,2-position, 1,3-position or 1,4-position with respect to each other, in another embodiment in 1,2-position or 1,3-position with respect to each other, in another embodiment in 1,2-position with respect to each other, in another embodiment in 1,4-position with respect to each other. In one embodiment, X is selected from the group consisting of $(C_1-C_6)$-alkanediyl, $(C_2-C_6)$-alkenediyl, $(C_3-C_7)$-cycloalkanediyl and $(C_1-C_6)$-alkanediyloxy, in another embodiment from $(C_1-C_6)$-alkanediyl, $(C_2-C_6)$-alkenediyl and $(C_1-C_6)$-alkanediyloxy, in another embodiment from $(C_1-C_6)$-alkanediyl, $(C_3-C_7)$-cycloalkanediyl and $(C_1-C_6)$-alkanediyloxy, in another embodiment from $(C_1-C_6)$-alkanediyl and $(C_1-C_6)$-alkanediyloxy, in another embodiment from $(C_1-C_6)$-alkanediyl, $(C_2-C_6)$-alkenediyl, $(C_2-C_6)$-alkynediyl and $(C_3-C_7)$-cycloalkanediyl, in another embodiment from $(C_1-C_6)$-alkanediyl, $(C_2-C_6)$-alkenediyl and $(C_3-C_7)$-cycloalkanediyl, in another embodiment from $(C_1-C_6)$-alkanediyl and $(C_2-C_6)$-alkenediyl, in another embodiment X is $(C_1-C_6)$-alkanediyl, in another embodiment X is $(C_2-C_6)$-alkenediyl, in another embodiment X is $(C_3-C_7)$-cycloalkanediyl and in another embodiment X is $(C_1-C_6)$-alkanediyloxy, all of which are optionally substituted as indicated. In one embodiment, a $(C_1-C_6)$-alkanediyl group present in X is a $(C_1-C_4)$-alkanediyl group, in another embodiment a $(C_1-C_3)$-alkanediyl group, in another embodiment a $(C_1-C_2)$-alkanediyl group. In one embodiment, the $(C_2-C_6)$-alkenediyl and $(C_2-C_6)$-alkynediyl groups representing X are $(C_2-C_4)$-alkenediyl and $(C_2-C_4)$-alkynediyl groups, in another embodiment $(C_2-C_3)$-alkenediyl and $(C_2-C_3)$-alkynediyl groups. In one embodiment, the $(C_3-C_7)$-cycloalkanediyl group representing X is a $(C_3-C_6)$-cycloalkanediyl group, in another embodiment a $(C_3-C_4)$-cycloalkanediyl group, in another embodiment a cyclopropanediyl group, in another embodiment a cyclohexanediyl group. Examples of groups X from which the respective group representing X may be selected in the above embodiments or from which X is selected in another embodiment of the invention are methylene, —CH(CH$_3$)— (ethane-1,1-diyl), —CH$_2$—CH$_2$— (ethane-1,2-diyl, 1,2-ethylene), —C(CH$_3$)$_2$— (1-methylethane-1,1-diyl), —CH$_2$—CH$_2$—CH$_2$— (propane-1,3-diyl, 1,3-propylene), —CH$_2$—CH(CH$_3$)— and —CH(CH$_3$)—CH$_2$— (propane-1,2-diyl, 1,2-propylene), which exemplify the group $(C_1-C_6)$-alkanediyl, —CH=CH— (ethene-1,2-diyl), —CH=CH—CH$_2$— and —CH$_2$—CH=CH— (prop-1-ene-1,3-diyl and prop-2-ene-1,3-diyl) and —CH=C(CH$_3$)— and —C(CH$_3$)=CH— (prop-1-ene-1,2-diyl), which exemplify the group $(C_2-C_6)$-alkenediyl, —C≡C— (ethynediyl) and —CH$_2$—C≡C— and —C≡C—CH$_2$— (prop-1-yne-1,3-diyl and prop-2-yne-1,3-diyl), which exemplify the group $(C_2-C_6)$-alkynediyl, cyclopropane-1,1-diyl, cyclopropane-1,2-diyl and cyclohexane-1,4-diyl, which exemplify the group $(C_3-C_7)$-cycloalkanediyl, —CH$_2$—O— (methyleneoxy), —CH$_2$—CH$_2$-β-(ethane-1,2-diyloxy), —CH(CH$_3$)—O— (ethane-1,1-diyloxy), —C(CH$_3$)$_2$—O— (1-methylethane-1,1-diyloxy), —CH$_2$—CH$_2$—CH$_2$—O— (propane-1,3-diyloxy) and —CH$_2$—CH$_2$—CH$_2$—CH$_2$—O— (butane-1,4-diyloxy), which exemplify the group $(C_1-C_6)$-alkanediyloxy, all of which are optionally substituted as indicated. Thus, in one embodiment X is selected from the group consisting of —CH$_2$—O—, —CH$_2$—CH$_2$—O—, —CH(CH$_3$)—O— and —C(CH$_3$)$_3$—O—, in another embodiment from —CH$_2$—O—, —CH$_2$—CH$_2$—O— and —CH(CH$_3$)—O—, in another embodiment from —CH$_2$—O— and —CH(CH$_3$)—O—, and in another embodiment X is —CH$_2$—O—, all of these groups being optionally substituted as indicated, and in which the oxygen atom is bonded to the group $R^2$. In one embodiment, the number of substituents which are optionally present in X, is 1, 2, 3 or 4, in another embodiment 1, 2 or 3, in another embodiment 1 or 2, in another embodiment 1, and in another embodiment the group X is not substituted by substituents selected from the group consisting of fluorine and hydroxyl. In one embodiment, the number of hydroxy substituents in X is not greater than 2, in another embodiment not greater than 1. In one embodiment, no more than one hydroxy substituent is present on an individual carbon atom in X. In one embodiment, hydroxy substituents are not present on carbon atoms which are part of a double bond in the group $(C_2-C_6)$-alkenediyl. In one embodiment, hydroxy substituents are not present on the carbon atom in the group $(C_1-C_6)$-alkanediyloxy which is bonded to the oxygen atom, in another embodiment no substituents are present on the carbon atom in the group $(C_1-C_6)$-alkanediyloxy which is bonded to the oxygen atom, i.e. in this latter embodiment all carbon atoms which are not linked to said oxygen atom are optionally substituted by one or more identical or different substituents selected from the group consisting of fluorine and hydroxyl. The double bond in the group $(C_2-C_6)$-alkenediyl can have E configuration or Z configuration. In one embodiment it has E configuration, in another embodiment it has Z configuration.

The 4-membered to 7-membered saturated or partially saturated, monocyclic or bicyclic heterocycle Y comprises the ring nitrogen atom depicted in formula I, which carries the carbonyl group bonded to the group X, as ring heteroatom, and in addition comprises 0, 1, 2 or 3, in one embodiment of the invention 0, 1 or 2, in another embodiment 0 or 1, in another embodiment 1 or 2, in another embodiment 1, in another embodiment 0, identical or different further ring heteroatoms selected from the group consisting of N, O and S, wherein one or two of the additional ring nitrogen atoms can carry a hydrogen atom or a $(C_1-C_4)$-alkyl substituent and one of the ring sulfur atoms can carry one or two oxo groups, and wherein the heterocycle is optionally substituted on one or more ring carbon atoms by identical or different $(C_1-C_4)$-alkyl substituents. In one embodiment, the additional heteroatoms which can be present in Y, are selected from the group consisting of N and O, in another embodiment from the group consisting of N and S, in another embodiment from the group consisting of O and S, in another embodiment they are N atoms, in another embodiment they are O atoms, and in another embodiment they are S atoms. As applies to the compounds of the formula I in general, ring heteroatoms in Y can be located in any positions, provided that the heterocyclic system is known in the art and is stable and suitable as a subgroup for the desired purpose of the compound of the formula I such as use as a drug substance. In one embodiment of the invention, two ring oxygen atoms in Y cannot be present in adjacent ring positions, in another embodiment two ring heteroatoms in Y selected from the group consisting of oxygen and sulfur cannot be present in adjacent ring positions, and in another embodiment two ring heteroatoms in Y, including the ring nitrogen atom which is depicted in formula I, cannot be present in adjacent ring positions. In case Y is saturated, the heterocycle Y does not contain double bonds within the ring. In case Y is partially unsaturated, i.e. the heterocycle Y contains one or more double bonds within the ring but is non-aromatic, in one embodiment the heterocycle contains one or two, in another embodiment one, double bonds within the ring which can be present in any suitable positions. In one embodiment, Y is saturated, in another embodiment Y is partially unsaturated.

In one embodiment, Y is a 4-membered to 6-membered, in another embodiment a 4-membered to 5-membered, in another embodiment a 5-membered to 6-membered, in another embodiment a 4-membered, in another embodiment a 5-membered, in another embodiment a 6-membered heterocycle which is saturated or partially unsaturated and monocyclic or bicyclic, and which is otherwise defined as indicated with respect to Y in general, as far as applicable. In one embodiment, the number of ring members in a monocyclic heterocycle representing Y is as indicated in the general definition of Y or in the aforementioned embodiments, and a bicyclic heterocycle representing Y is 6-membered to 7-membered, in another embodiment 6-membered, in another embodiment 7-membered. In bicyclic heterocycles representing Y the bridgehead atoms can be nitrogen atoms, which are any of the ring nitrogen atoms which can be present in addition to the ring nitrogen atom depicted in formula I, and/or ring carbon atoms. In one embodiment, one of the bridgehead atoms in a bicyclic heterocycle representing Y is a carbon atom and the other is a carbon atom or a nitrogen atom, in another embodiment both bridgehead atoms are carbon atoms. Examples of bicyclic ring systems from which bicyclic heterocycles representing Y are chosen in one embodiment, are bicyclo[3.1.0], bicyclo[3.2.0], bicyclo[4.1.0], bicyclo[2.2.1] and bicyclo[2.1.1] ring systems which comprise the ring nitrogen atom depicted in formula and additional ring heteroatoms which are optionally present in Y, and which are saturated or partially unsaturated and are otherwise defined as indicated with respect to Y in general, as far as applicable. In one embodiment, a bicyclic heterocycle representing Y is saturated. In one embodiment Y is a monocyclic heterocycle, in another embodiment Y is a bicyclic heterocycle. In one embodiment, the number of $(C_1-C_4)$-alkyl substituents which are optionally present on ring carbon atoms in Y, is one, two, three or four, in another embodiment one or two, and in another embodiment Y is not substituted on ring carbon atoms by $(C_1-C_4)$-alkyl substituents.

In one embodiment, Y is a 4-membered to 7-membered saturated monocyclic or bicyclic heterocycle which, in addition to the ring nitrogen atom shown in formula I, contains 0 or 1 ring heteroatoms selected from the group consisting of N, O and S, where the additional ring nitrogen atom may carry a hydrogen atom or a $(C_1-C_4)$-alkyl substituent and the ring sulfur atom may carry one or two oxo groups and where the heterocycle is optionally substituted at one or more ring carbon atoms by identical or different $(C_1-C_4)$-alkyl substituents. In another embodiment, Y is a 4-membered to 6-membered, saturated, monocyclic heterocycle which does not comprise further ring heteroatoms in addition to the ring nitrogen atom depicted in formula I, wherein the ring is optionally substituted on one or more ring carbon atoms by identical or different $(C_1-C_4)$-alkyl substituents. In another embodiment, Y is selected from one or more of the heterocycles azetidine, pyrrolidine and piperidine, the ring nitrogen atom of which is the ring nitrogen atom of Y depicted in formula I which carries the carbonyl group bonded to the group X, wherein these heterocycles are optionally substituted on ring carbon atoms by one or more identical or different $(C_1-C_4)$-alkyl substituents, and in another embodiment these heterocycles do not carry alkyl substituents.

The group $R^4$—O—C(O)— can be bonded to the heterocycle Y in any suitable position. In one embodiment, the group $R^4$—O—C(O)— is bonded to a ring carbon atom of Y in any position, in another embodiment it is bonded to a ring carbon atom in Y which is in a ring position adjacent to the ring nitrogen atom in Y depicted in formula I, in another embodiment it is bonded to a ring carbon atom in Y which is adjacent to said ring nitrogen atom or separated from said ring nitrogen atom by one or two ring members, in another embodiment it is bonded to a ring carbon atom which is adjacent to said ring nitrogen or separated from said ring nitrogen atom by at least one ring member, in another embodiment it is bonded to a ring carbon atom in Y which is separated from said ring nitrogen atom by one or two ring members, and in another embodiment it is bonded to a ring carbon atom which is separated from said ring nitrogen atom by at least one ring member. For example, in case of a heterocycle Y which does not contain further ring heteroatoms in addition to the nitrogen atom depicted in formula I and in which said ring nitrogen atom thus is in position 1 of the heterocycle, in one embodiment the group $R^4$—O—C(O)— is bonded to a ring carbon atom in any position, in another embodiment it is bonded in position 2, in another embodiment in position 3, in another embodiment in position 4, in another embodiment in position 2 or 3, in another embodiment in position 3 or 4, in another embodiment in position 2, 3 or 4. In one embodiment, in a partially unsaturated heterocycle Y the group $R^4$—O—C(O)— is bonded to a ring atom which is not part of a double bond. In one embodiment, in case of a bicyclic heterocycle Y the group $R^4$—O—C(O)— is bonded to a ring atom which is not a bridgehead atom. The group Y can be present on the heterocycle Y in any stereochemical position, for example in endo position or exo position in the case or a bicyclic ring Y, or in cis position or in trans position with respect to an substituent on Y, or on a carbon atom having S configuration or a carbon atom having R configuration. For example, in the case of a ring Y which is selected from the group consisting of azetidine, pyrrolidine, piperidine and perhydroazepine, the ring nitrogen atom of which is the ring nitrogen atom of Y depicted in formula I, and which carries the group $R^4$—O—C(O)— in position 2, in one embodiment the carbon atom carrying the group $R^4$—O—C(O)— is present in S configuration. Examples of the grouping $R^{40}$—C(O)—Y— from which this grouping in the compounds of the formula I is chosen in one embodiment, are 2-hydroxycarbonylazetidin-1-yl, 2-(($C_1-C_4$)-alkyloxycarbonyl)azetidin-1-yl, (S)-2-hydroxycarbonylazetidin-1-yl, (S)-2-($C_1-C_4$)-alkyloxycarbonyl)azetidin-1-yl, 3-hydroxycarbonylazetidin-1-yl, 3-(($C_1-C_4$)-alkyloxycarbonyl)azetidin-1-yl, 2-hydroxycarbonylpyrrolidin-1-yl, 2-($C_1-C_4$)-alkyloxycarbonyl)pyrrolidin-1-yl, (S)-2-hydroxycarbonylpyrrolidin-1-yl, (S)-2-(($C_1-C_4$)-alkyloxycarbonyl)pyrrolidin-1-yl, 3-hydroxycarbonylpyrrolidin-1-yl, 3-(($C_1-C_4$)-alkyloxycarbonyl)pyrrolidin-1-yl, 2-hydroxycarbonylpiperidin-1-yl, 2-(($C_1-C_4$)-alkyloxycarbonyl)piperidin-1-yl, (S)-2-hydroxycarbonylpiperidin-1-yl, (S)-2-(($C_1-C_4$)-alkyloxycarbonyl)piperidin-1-yl, 3-hydroxycarbonylpiperidin-1-yl, 3-(($C_1-C_4$)-alkyloxycarbonyl)piperidin-1-yl, 4-hydroxycarbonylpiperidin-1-yl, 4-(($C_1-C_4$)-alkyloxycarbonyl)piperidin-1-yl, 2-hydroxycarbonylperhydroazepin-1-yl, 2-(($C_1-C_4$)-alkyloxycarbonyl)perhydroazepin-1-yl, (S)-2-hydroxycarbonylperhydroazepin-1-yl, (S)-2-($C_1-C_4$)-alkyloxycarbonyl)perhydroazepin-1-yl, 3-hydroxycarbonylperhydroazepin-1-yl, 3-(($C_1-C_4$)-alkyloxycarbonyl)perhydroazepin-1-yl, 4-hydroxycarbonylperhydroazepin-1-yl, 4-(($C_1$-$C_4$)-alkyloxycarbonyl)perhydroazepin-1-yl, 2-hydroxycarbonylmorpholin-4-yl, 2-(($C_1$-$C_4$)-alkyloxycarbonyl)morpholin-4-yl, 3-hydroxycarbonylmorpholin-4-yl, 3-(($C_1$-$C_4$)-alkyloxycarbonyl)morpholin-4-yl, 2-hydroxycarbonylthiomorpholin-4-yl, 2-(($C_1$-$C_4$)-alkyloxycarbonyl)thiomorpholin-4-yl, 3-hydroxycarbonylthiomorpholin-4-yl, 3-(($C_1$-$C_4$)-alkyloxycarbonyl)thiomorpholin-4-yl, 2-hydroxycarbonyl-1,1-dioxothiomorpholin-4-yl, 2-(($C_1$-$C_4$)-alkyloxycarbonyl)-1,1-dioxothiomorpholin-4-yl, 3-hydroxycarbonyl-1,1-dioxothiomorpholin-4-yl, 3-(($C_1$-$C_4$)-alkyloxycarbonyl)-1,1-dioxothiomorpholin-4-yl, 2-hydroxycarbonyl-4-methylpiperazin-1-yl, 2-(($C_1$-$C_4$)-alkyloxycarbonyl)-4-methylpiperazin-1-yl, 3-hydroxycarbonyl-4-methylpiperazin-1-yl, 3-(($C_1$-$C_4$)-alkyloxycarbonyl)-1-methylpiperazin-1-yl.

In one embodiment of the invention, the number t is selected from the group consisting of 0, 1 or 2, in another embodiment from 0 or 1, in another embodiment from 1, 2 or 3, in another embodiment from 1 or 2, in another embodiment t is 0, in another embodiment t is 1. In one embodiment, $R^1$ is selected from the group consisting of ($C_1$-$C_6$)-alkyl, ($C_3$-$C_7$)-cycloalkyl-$C_tH_{2t}$— and Het-$C_tH_{2t}$—, in another embodiment from ($C_1$-$C_6$)-alkyl and ($C_3$-$C_7$)-cycloalkyl-$C_tH_{2t}$—, in another embodiment, $R^1$ is ($C_1$-$C_6$)-alkyl, in another embodiment, $R^1$ is ($C_3$-$C_7$)-cycloalkyl-$C_tH_{2t}$—, and in another embodiment, $R^1$ is Het-$C_tH_{2t}$—. In one embodiment, $R^1$ is ($C_3$-$C_7$)-cycloalkyl-$C_tH_{2t}$— in which t is selected from the group consisting of 0, 1 and 2, in another embodiment, $R^1$ is ($C_3$-$C_7$)-cycloalkyl-$C_tH_{2t}$— in which t is selected from the group consisting of 0 and 1, in another embodiment, $R^1$ is ($C_3$-$C_7$)-cycloalkyl-$CH_2$—, in another embodiment, $R^1$ is ($C_3$-$C_7$)-cycloalkyl, in another embodiment, $R^1$ is Het-$C_tH_{2t}$— in which t is selected from the group consisting of 0, 1 and 2, in another embodiment, $R^1$ is Het-$C_tH_{2t}$— in which t is selected from the group consisting of 0 and 1, in another embodiment, $R^1$ is Het-$CH_2$—, in another embodiment, $R^1$ is Het. In one embodiment, a ($C_1$-$C_6$)-alkyl group which represents $R^1$ is ($C_2$-$C_6$)-alkyl, in another embodiment ($C_2$-$C_5$)-alkyl, in another embodiment ($C_3$-$C_5$)-alkyl. In one embodiment, a ($C_2$-$C_6$)-alkenyl group and a ($C_2$-$C_6$)-alkynyl group representing $R^1$ are $C_3$-$C_6$)-alkenyl and ($C_3$-$C_6$)-alkynyl, respectively, in another embodiment ($C_3$-$C_4$)-alkenyl and ($C_3$-$C_4$)-alkynyl, respectively. In one embodiment, a ($C_3$-$C_7$)-cycloalkyl group which is present in $R^1$ is ($C_3$-$C_6$)-cycloalkyl, in another embodiment ($C_3$-$C_5$)-cycloalkyl, in another embodiment ($C_3$-$C_4$)-cycloalkyl, in another embodiment cyclopropyl. In one embodiment, a group Het which represents $R^1$ is a 4-membered to 6-membered, in another embodiment a 4-membered or 5-membered, in another embodiment a 4-membered, saturated monocyclic heterocycle which is attached via a ring carbon atom and which has 1 or 2 identical or different ring heteroatoms, in another embodiment 1 ring heteroatom, which are/is selected from the group consisting of N, O and S, in another embodiment from O and S, and which, in another embodiment, represent O atoms. In one embodiment, a group Het which represents $R^1$ is an oxetanyl group, for example an oxetan-3-yl group. In one embodiment, the number of substituents optionally present at a group Het representing $R^1$ is one, two or three, in another embodiment one or two, in another embodiment one, and in another embodiment such a group Het is unsubstituted. In one embodiment, a ($C_1$-$C_4$)-alkyl substituent present at a group Het representing $R^1$ is a methyl group.

In one embodiment of the invention, the number of ring heteroatoms in an aromatic heterocycle representing $R^2$ is 1 or 2, in another embodiment, it is 1. In one embodiment of the invention, $R^2$ is selected from the group consisting of phenylene and a divalent residue of an aromatic, 6-membered monocyclic heterocycle which comprises 1, 2 or 3 ring nitrogen atoms, in another embodiment 1 or 2 ring nitrogen atoms, in another embodiment 1 ring nitrogen atom, where one of the ring nitrogen atoms can carry a substituent $R^{21}$ which is oxy, i.e. where one of the ring nitrogen atoms can be oxidized to the N-oxide, and where the phenylene and divalent residue of an aromatic heterocycle are optionally substituted on one or more ring carbon atoms by identical or different substituents $R^{22}$. In another embodiment, $R^2$ is phenylene, wherein the phenylene is optionally substituted on one or more ring atoms by identical or different substituents $R^{22}$, and in another embodiment $R^2$ is pyridinediyl, wherein the ring nitrogen atom can carry a substituent $R^{21}$ which is oxy, i.e. wherein the ring nitrogen atom can be oxidized to the N-oxide, and wherein the pyridinediyl is optionally substituted on one or more ring carbon atoms by identical or different substituents $R^{22}$. In another embodiment, $R^2$ is a divalent residue of an aromatic 5-membered heterocycle which comprises 1, 2 or 3 identical or different ring heteroatoms selected from the group consisting of N, O and S, wherein one of the ring nitrogen atoms can carry a hydrogen atom or a substituent $R^{21}$, and wherein the divalent residue of an aromatic heterocycle is optionally substituted on one or more ring carbon atoms by identical or different substituents $R^{22}$. In one embodiment, a residue of an aromatic heterocyclic group representing $R^2$ is selected from the group consisting of furandiyl, thiophenediyl, oxazolediyl, thiazolediyl, pyridinediyl, pyridazinediyl, pyrimidinediyl and pyrazinediyl, in another embodiment from furandiyl, thiophenediyl, thiazolediyl, pyridinediyl, pyridazinediyl, pyrimidinediyl and pyrazinediyl, in another embodiment from furandiyl, thiophenediyl, pyridinediyl, pyridazinediyl, pyrimidinediyl and pyrazinediyl, in another embodiment from furandiyl, thiophenediyl, pyridinediyl and pyrimidinediyl, in another embodiment from furandiyl, thiophenediyl and pyridinediyl, which are all optionally substituted as indicated with respect to $R^2$.

The ring carbon atoms via which the phenylene group and the divalent residue of an aromatic heterocycle representing $R^2$ are bonded to the oxazolopyrimidine ring and to the group X, can be in any positions. A phenylene group representing $R^2$ can be 1,2-phenylene, i.e. the oxazolopyrimidine ring and the group X can, be bonded in 1,2-position, or ortho position, with respect to each other, it can be 1,3-phenylene, i.e. the oxazolopyrimidine ring and the group X can be bonded in 1,3-position, or meta position, with respect to each other, and it can be 1,4-phenylene, i.e. the oxazolopyrimidine ring and the group X can be bonded in 1,4-position, or para position, with respect to each other. In one embodiment, a phenylene group representing $R^2$ is selected from the group consisting of 1,3-phenylene and 1,4-phenylene, in another embodiment it is 1,3-phenylene, and in another embodiment it is 1,4-phenylene, which groups are all optionally substituted as indicated with respect to $R^2$. In one embodiment, $R^2$ is selected from one or more of the groups phenylene, furan-2,5-diyl, thiophene-2,4-diyl, thiophene-2,5-diyl, pyridine-2,4-diyl, pyridine-2,5-diyl, pyridine-3,5-diyl, pyridine-2,6-diyl and pyrimidine-2,5-diyl, in another embodiment from the groups furan-2,5-diyl, thiophene-2,4-diyl, thiophene-2,5-diyl, pyridine-2,4-diyl, pyridine-2,5-diyl, pyridine-2,6-diyl and pyrimidine-2,5-diyl, in another embodiment from pyridine-2,4-diyl, pyridine-2,5-diyl, pyridine-3,5-diyl and pyridine-2,6-diyl, in another embodiment from phenylene, pyridine-2,4-diyl, pyridine-2,5-diyl, pyridine-3,5-diyl and pyridine-2,6- diyl, which all are optionally substituted as indicated with respect to $R^2$. In one embodiment, the number of substituents $R^{22}$ which are optionally present on ring carbon atoms in $R^2$, is 1, 2, 3, 4 or 5, in another embodiment 1, 2, 3 or 4, in another embodiment 1, 2 or 3, in another embodiment 1 or 2, in another embodiment 1. Ring nitrogen atoms in $R^2$ which do not carry a substituent $R^{22}$ carry a hydrogen atom.

In one embodiment of the invention, $R^3$ is selected from the group consisting of $(C_1-C_6)$-alkyl, $(C_2-C_6)$-alkenyl and $(C_2-C_6)$-alkynyl, in another embodiment, $R^3$ is $(C_1-C_6)$-alkyl, in another embodiment, $R^3$ is $(C_2-C_5)$-alkyl, and in another embodiment, $R^3$ is $(C_1-C_4)$-alkyl, with the proviso that $R^3$ may not be an alkyl group if A is S. In another embodiment, $R^3$ is selected from the group consisting of $(C_3-C_7)$-cycloalkyl-$C_uH_{2u}$— and Het-$C_vH_{2v}$—, in another embodiment, $R^3$ is $(C_3-C_7)$-cycloalkyl-$C_uH_{2u}$—, and in another embodiment, $R^3$ is Het-$C_vH_{2v}$—, where in this embodiment u and v independently of one another are selected from the group consisting of 1 and 2. In one embodiment, u is 1, in another embodiment, u is 2. In one embodiment, v is 1, in another embodiment, v is 2. In one embodiment, the group $(C_3-C_7)$-cycloalkyl-$C_uH_{2u}$-which represents $R^3$ is selected from the group consisting of cyclopropyl-$C_uH_{2u}$—, cyclobutyl-$C_uH_{2u}$— and cyclopentyl-$C_uH_{2u}$—, and the group Het-$C_vH_{2v}$—, which represents $R^3$ is tetrahydrofuranyl-$C_vH_{2v}$—. In one embodiment, $R^3$ is selected from the group consisting of cyclopropyl-$C_uH_{2u}$—, cyclobutyl-$C_uH_{2u}$— and cyclopentyl-$C_uH_{2u}$—.

In one embodiment, $R^3$ is selected from the group consisting of $(C_3-C_7)$-cycloalkyl-$C_uH_{2u}$— and Het-$C_vH_{2v}$—, or $R^3$ is a radical of a saturated or unsaturated, 3-membered to 10-membered, monocyclic or bicyclic ring which contains 0, 1, 2, 3 or 4 identical or different ring heteroatoms selected from the group consisting of N, O and S, wherein one or two of the ring nitrogen atoms may carry a hydrogen atom or a $(C_1-C_4)$-alkyl substituent and one or two of the ring sulfur atoms may carry one or two oxo groups, and where the radical of a ring is optionally substituted at one or more ring carbon atoms by identical or different substituents $R^{31}$, and in another embodiment $R^3$ is a radical of a saturated or unsaturated, 3-membered to 10-membered, monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups, and where the residue of a ring is optionally substituted at one or more ring carbon atoms by identical or different substituents $R^{31}$. In one embodiment, the number of ring heteroatoms in the ring representing $R^3$ is 0, 1, 2 or 3, in another embodiment 0, 1 or 2, in another embodiment 0 or 1, in another embodiment 0, in another embodiment it is 1, 2, 3 or 4, in another embodiment 1, 2 or 3, in another embodiment 1 or 2, in another embodiment 1. Thus, the radical of the ring which represents $R^3$ may be carbocyclic or heterocyclic. In one embodiment, the ring heteroatoms in $R^3$ are selected from the group consisting of N and O, in another embodiment from N and S, in another embodiment from O and S, in another embodiment they are N, where ring nitrogen atoms may carry a hydrogen atom or a $(C_1-C_4)$-alkyl substituent as occurs in saturated or partially unsaturated heterocycles or in 5-membered aromatic rings in heterocycles such as pyrrole or benzimidazole, for example, or may not carry a hydrogen atom or a $(C_1-C_4)$-alkyl substituent as occurs in aromatic heterocycles such as imidazole or pyridine, for example. In a radical of a heterocycle representing $R^3$ which contains one or more ring sulfur atoms, in one embodiment one of the ring sulfur atoms is non-oxidized or carries one or two oxo groups, and all other ring sulfur atoms are non-oxidized. The radical of a monocyclic or bicyclic ring representing $R^3$ may be bonded to the group A via any suitable ring carbon atom or ring nitrogen atom. In one embodiment it is bonded via a ring carbon atom, in another embodiment it is bonded via a ring carbon atom or, in case A is NH, via a ring nitrogen atom, and in another embodiment it is bonded via a ring nitrogen atom. The radical of a monocyclic or bicyclic ring representing $R^3$ may be unsaturated and in this case may contain 1, 2, 3, 4 or 5, or 1, 2, 3 or 4, or 1, 2 or 3, or 1 or 2, or 1, double bonds within the ring and may be aromatic or non-aromatic in any of the two rings, or it may be saturated and in this latter case contain no double bonds within the ring. In one embodiment, the radical of the ring representing $R^3$ is saturated or aromatic, in another embodiment it is saturated, and in another embodiment it is aromatic. In one embodiment, the radical of the 3-membered or 4-membered ring representing $R^3$ is saturated. If $R^3$ comprises ring nitrogen atoms which can carry a hydrogen atom or a $(C_1-C_4)$-alkyl substituent, one of such ring nitrogen atoms or two of such ring nitrogen atoms may be present. In one embodiment, the number of optional substituents $R^{31}$ on ring carbon atoms in the ring representing $R^3$ is 1, 2, 3, 4, 5 or 6, in another embodiment 1, 2, 3, 4 or 5, in another embodiment 1, 2, 3 or 4, in another embodiment 1, 2 or 3, in another embodiment 1 or 2, in another embodiment 1.

The ring which can represent $R^3$ may be 3-membered, 4-membered, 5-membered, 6-membered, 7-membered, 8-membered, 9-membered or 10 membered. In one embodiment, $R^3$ is 4-membered to 10-membered, in another embodiment 4-membered to 9-membered, in another embodiment 4-membered to 8-membered, in another embodiment 4-membered to 7-membered, in another embodiment 5-membered to 7-membered, in another embodiment 5-membered or 6-membered, in another embodiment 6-membered, in another embodiment 8-membered to 10-membered, in another embodiment 9-membered to 10-membered. In one embodiment, a 3-membered ring representing $R^3$ does not contain any ring heteroatoms. In one embodiment, $R^3$ is monocyclic, in another embodiment bicyclic. In one embodiment, a bicyclic group representing $R^3$ is at least 7-membered. Among others, the radical of a ring representing $R^3$ can be a cycloalkyl group, a phenyl group, a naphthyl group, a radical of an unsaturated, aromatic or non-aromatic heterocyclic group or a radical of a saturated heterocyclic group, which all are optionally substituted on ring carbon atoms and ring nitrogen atoms as specified with respect to $R^3$. As far as applicable, all explanations given above with respect to such groups apply correspondingly to $R^3$. Another example of groups which may represent $R^3$ are cycloalkenyl groups such as $(C_5-C_7)$-cycloalkenyl groups, which may be bonded via any ring carbon atom and are optionally substituted as specified with respect to $R^3$. In one embodiment, optional substituents $R^{31}$ on a cycloalkenyl group representing $R^3$ are selected from the group consisting of fluorine and $(C_1-C_4)$-alkyl. In one embodiment, cycloalkenyl groups contain one double bond within the ring, which double bond may be present in any position. Examples of cycloalkenyl are cyclopentenyl including cyclopent-1-enyl, cyclopent-2-enyl and cyclopent-3-enyl, cyclohexenyl including cyclohex-1-enyl, cyclohex-2-enyl and cyclohex-3-enyl, and cycloheptenyl including cyclohept-1-enyl, cyclohept-2-enyl, cyclopent-3-enyl and cyclohept-4-enyl. Examples of radicals of rings from which $R^3$ is chosen in one embodiment of the invention are cyclobutyl, cyclopentyl, cyclohexyl, phenyl, oxetanyl including oxetan-3-yl, tetrahydrofuranyl including tetrahydrofuran-3-yl, tetrahydrothiophenyl including tetrahydrothiophen-3-yl, tetrahydropyranyl including tetrahydropyran-4-yl, azetidinyl including azetidin-1-yl, pyrrolidinyl, piperidinyl, imidazolidinyl, piperazinyl, morpholinyl including morpholin-1-yl, thiomorpholinyl, furanyl including furan-3-yl, thiophenyl including thiophen-3-yl, pyrazolyl including pyrazol-3-yl, imidazolyl, thiazolyl including thiazol-2-yl, pyridinyl including pyridin-2-yl, pyridin-3-yl and pyridin-4-yl, pyridazinyl including pyridazin-3-yl, where in all of them, if applicable, one or two of the ring nitrogen atoms may carry a hydrogen atom or $(C_1-C_4)$-alkyl, and where all of them are optionally substituted at one or more ring carbon atoms by identical or different substituents $R^{31}$, and where in all of them, if applicable, a ring sulfur atom may be non-oxidized, i.e. be present as a sulfur atom, or carry one or two oxo groups, i.e. be present in the form of a sulfoxide or sulfone.

In one embodiment, $R^3$ is selected from the group consisting of phenyl and a radical of a saturated or unsaturated 3-membered to 7-membered, monocyclic ring, in another embodiment from phenyl and a radical of a saturated or unsaturated 5-membered to 7-membered, monocyclic ring, in another embodiment from phenyl, pyridinyl and a radical of a saturated 3-membered to 7-membered, monocyclic ring, in another embodiment from phenyl, pyridinyl and a radical of a saturated 5-membered to 7-membered, monocyclic ring, in another embodiment from phenyl and pyridinyl, in another embodiment from phenyl and a radical of a saturated 3-membered to 7-membered, monocyclic ring, in another embodiment from phenyl and a radical of a saturated 5-membered to 7-membered, monocyclic ring, in another embodiment from one or more of the groups phenyl, cyclobutyl, cyclopentyl, cyclohexyl and pyridinyl, in another embodiment from one or more of the groups phenyl, cyclopentyl and cyclohexyl, in another embodiment from one or both of the groups phenyl and cyclohexyl, wherein in all these embodiments the monocyclic ring contains 1 or 2 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups, and where the phenyl, the pyridinyl, the radical of a ring, the cyclobutyl, the cyclopentyl and the cyclohexyl are optionally substituted at one or more ring carbon atoms by identical or different substituents $R^{31}$, and where pyridinyl includes pyridin-2-yl, pyridin-3-yl and pyridin-4-yl. In another embodiment, $R^3$ is phenyl which is optionally substituted by one or more identical or different substituents $R^{31}$.

In one embodiment of the invention, the number z is selected from the group consisting of 0 and 1, in another embodiment it is 0, in another embodiment it is 1. In one embodiment of the invention, the group $R^4$ is selected from the group consisting of hydrogen and $(C_1-C_4)$-alkyl, in another embodiment, $R^4$ is selected from the group consisting of hydrogen, methyl, ethyl, n-propyl, n-butyl and isopropyl, in another embodiment from hydrogen, methyl and ethyl, in another embodiment, $R^4$ is hydrogen, in another embodiment, $R^4$ is $(C_1-C_4)$-alkyl, in another embodiment, $R^4$ is methyl and in another embodiment, $R^4$ is ethyl. In one embodiment, a $(C_3-C_7)$-cycloalkyl group present in $R^4$ is $(C_3-C_6)$-cycloalkyl, in another embodiment, it is cyclopropyl.

In one embodiment of the invention, the number w is selected from the group consisting of 0 and 1, in another embodiment it is 0, in another embodiment it is 1. In one embodiment, a $(C_3-C_7)$-cycloalkyl group which is present in $R^{21}$ is $(C_3-C_6)$-cycloalkyl, in another embodiment $(C_3-C_6)$-cycloalkyl, in another embodiment cyclopropyl. In one embodiment, $R^{21}$ is selected from the group consisting of $(C_1-C_4)$-alkyl and oxy, in another embodiment, $R^{21}$ is $(C_1-C_4)$-alkyl, in another embodiment it is $(C_1-C_3)$-alkyl, in another embodiment it is methyl and in another embodiment it is oxy.

In one embodiment of the invention, the substituents $R^{22}$ optionally present at the group $R^2$ are selected from the group consisting of halogen, hydroxyl, $(C_1-C_4)$-alkyl-, $(C_1-C_4)$-alkyloxy-, $(C_1-C_4)$-alkyl-$S(O)_m$—, amino, nitro and cyano, in another embodiment from halogen, hydroxyl, $(C_1-C_4)$-alkyl-, $(C_1-C_4)$-alkyloxy-, amino and cyano, in another embodiment from halogen, hydroxyl, $(C_1-C_4)$-alkyl- and $(C_1-C_4)$-alkyloxy-, in another embodiment from fluorine, chlorine, hydroxyl, $(C_1-C_4$-alkyl- and $(C_1-C_4)$-alkyloxy-, in another embodiment from fluorine, chlorine and $(C_1-C_4)$-alkyl-, and in another embodiment they are $(C_1-C_4)$-alkyl substituents.

In one embodiment, 1, 2 or 3 of the substituents $R^{22}$, in another embodiment 1 or 2 of the substituents $R^{22}$, and in another embodiment 1 of the substituents $R^{22}$, which are optionally present on the group $R^2$, are defined as in the general definition of $R^{22}$ and thus are selected from the group consisting of halogen, hydroxyl, $(C_1-C_4)$-alkyl-, $(C_1-C_4)$-alkyl-$S(O)_m$—, amino, nitro, cyano, hydroxycarbonyl, $(C_1-C_4)$-alkyloxycarbonyl, aminocarbonyl and aminosulfonyl, and any further substituents $R^{22}$ which are optionally present at the group $R^2$, for example 1, 2 or 3 further substituents $R^{22}$, or 1 or 2 further substituents $R^{22}$, or 1 further substituent $R^{22}$, are selected from the group consisting of halogen, hydroxyl, $(C_1-C_4)$-alkyl-, $(C_1-C_4)$-alkyloxy-, $(C_1-C_4)$-alkyl-$S(O)_m$—, amino, nitro and cyano, where all alkyl groups independently of each other are optionally substituted by one or more fluorine substituents as generally applies to alkyl groups. In one embodiment, the substituents $R^{22}$ which are optionally present at the group $R^2$ and which in the aforementioned embodiment are defined as in the general definition of $R^{22}$, for example 1 or 2 such substituents $R^{22}$, or 1 such substituent $R^{22}$, are selected from the group consisting of halogen, hydroxyl, $(C_1-C_4)$-alkyl-, $(C_1-C_4)$-alkyloxy-, $(C_1-C_4)$-alkyl-$S(O)_m$—, amino, nitro and cyano. In one embodiment, the substituents $R^{22}$ which are optionally present at the group $R^2$ and which in the aforementioned embodiment are defined as in the general definition of $R^{22}$, for example 1 or 2 such substituents $R^{22}$, or 1 such substituent $R^{22}$, are not located at ring carbon atoms within the group $R^2$ which is adjacent to the atom via which the group $R^2$ is attached to the oxazolopyrimidine ring shown in formula I. In one embodiment, the further substituents $R^{22}$ which are optionally present at the group $R^2$, for example 1, 2 or 3 further substituents $R^{22}$, or 1 or 2 further substituents $R^{22}$, or 1 further substituent $R^{22}$, are selected from the group consisting of halogen, hydroxyl, $C_1-C_4)$-alkyl-, $(C_1-C_4)$-alkyloxy-, amino, cyano, in another embodiment from halogen, hydroxy, $(C_1-C_4)$-alkyl- and $C_1-C_4)$-alkyloxy-, in another embodiment from halogen, $(C_1-C_4)$-alkyl- and $(C_1-C_4)$-alkyloxy-, in another embodiment from halogen and $(C_1-C_4)$-alkyl-, wherein in all these embodiments all alkyl groups independently of each other are optionally substituted by one or more fluorine substituents.

In one embodiment of the invention, $R^{31}$ is selected from the group consisting of halogen, $(C_1-C_4)$-alkyl, $(C_3-C_7)$-cycloalkyl, hydroxyl, $(C_1-C_4)$-alkyloxy, oxo, $(C_1-C_4)$-alkyl-S$(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, $(C_1-C_4)$-alkylcarbonyl, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxyl, $(C_1-C_4)$-alkyloxy, oxo, $(C_1-C_4)$-alkyl-S$(O)_m$—, amino, $(C_1-C_4)$-alkylamino, alkyl)amino, cyano, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxyl, $(C_1-C_4)$-alkyloxy, oxo, $(C_1-C_4)$-alkyl-$S(O)_m$—, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxyl, $(C_1-C_4)$-alkyloxy, oxo, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxyl, $(C_1-C_4)$-alkyloxy, oxo, amino, $(C_1-C_4)$-alkylamino and di$((C_1-C_4)$-alkyl)amino, in another embodiment from halogen, $(C_1-C_4)$-alkyl, $(C_3-C_7)$-cycloalkyl, $(C_1-C_4)$-alkyloxy and di$((C_1-C_4)$-alkyl)amino, in another embodiment from halogen, $(C_1-C_4)$-alkyl, $(C_3-C_7)$-cycloalkyl, hydroxyl and $(C_1-C_4)$-alkyloxy, in another embodiment from halogen, $(C_1-C_4)$-alkyl and $(C_1-C_4)$-alkyloxy, in another embodiment from fluorine, chlorine, $(C_1-C_4)$-alkyl, $(C_3-C_7)$-cycloalkyl, hydroxyl and $(C_1-C_4)$-alkyloxy, where in all these embodiments all alkyl groups independently of one another are optionally substituted by one or more fluorine substituents.

In one embodiment, the optional substituents $R^{31}$ at the radical of a saturated or nonaromatic unsaturated ring representing $R^3$ are selected from the group consisting of halogen, $(C_1-C_4)$-alkyl, $(C_3-C_7)$-cycloalkyl, hydroxyl, $(C_1-C_4)$-alkyloxy, $(C_1-C_4)$-alkyl-$S(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, $(C_1-C_4)$-alkylcarbonyl, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxyl, $(C_1-C_4)$-alkyloxy, $(C_1-C_4)$-alkyl-$S(O)_m$—, amino, $(C_1-C_4)$-alkylamino, di$((C_1-C_4)$-alkyl)amino, cyano, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxyl, $(C_1-C_4)$-alkyloxy, $(C_1-C_4)$-alkyl-$S(O)_n$—, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxyl, $(C_1-C_4)$-alkyloxy, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxyl, $(C_1-C_4)$-alkyloxy, amino, $(C_1-C_4)$-alkylamino and di$((C_1-C_4)$-alkyl)amino, in another embodiment from halogen, $(C_1-C_4)$-alkyl, $(C_3-C_7)$-cycloalkyl, $(C_1-C_4)$-alkyloxy and di$((C_1-C_4)$-alkyl)amino, in another embodiment from halogen, $(C_1-C_4)$-alkyl, $(C_3-C_7)$-cycloalkyl, hydroxyl and $(C_1-C_4)$-alkyloxy, in another embodiment from halogen, $(C_1-C_4)$-alkyl and $(C_1-C_4)$-alkyloxy, in another embodiment from fluorine, chlorine, $(C_1-C_4)$-alkyl, $(C_3-C_7)$-cycloalkyl, hydroxyl and $(C_1-C_4)$-alkyloxy, where in all these embodiments all alkyl groups independently of one another are optionally substituted by one or more fluorine substituents.

In one embodiment, the optional substituents $R^{31}$ at the radical of a saturated or nonaromatic unsaturated ring representing $R^3$ are selected from the group consisting of halogen, $(C_1-C_4)$-alkyl, $(C_3-C_7)$-cycloalkyl, hydroxyl, $(C_1-C_4)$-alkyloxy, oxo, $(C_1-C_4)$-alkyl-$S(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino and cyano, in another embodiment from halogen, $(C_1-C_4)$-alkyl, $(C_3-C_7)$-cycloalkyl, hydroxyl, $(C_1-C_4)$-alkyloxy, oxo, amino, $(C_1-C_4)$-alkylamino, di$((C_1-C_4)$-alkyl)amino and cyano, in another embodiment from halogen, $(C_1-C_4)$-alkyl, $(C_3-C_7)$-cycloalkyl, hydroxyl, $(C_1-C_4)$-alkyloxy and oxo, in another embodiment from halogen, $(C_1-C_4)$-alkyl, hydroxyl, $(C_1-C_4)$-alkyloxy and oxo, in another embodiment from fluorine, chlorine, $(C_1-C_4)$-alkyl, hydroxyl, $(C_1-C_4)$-alkyloxy and oxo, in another embodiment from $(C_1-C_4)$-alkyl, hydroxyl and oxo, in another embodiment from alkyl and hydroxyl, and in another embodiment they are $(C_1-C_4)$-alkyl, where in all these embodiments all alkyl groups independently of one another are optionally substituted by one or more fluorine substituents. If the radical of a ring representing $R^3$ contains any oxo groups as substituents $R^{31}$, in one embodiment not more than two such oxo substituents are present, and in another embodiment not more than one such oxo substituent is present.

In one embodiment of the invention, the ring heteroatoms in Het are selected from the group consisting of N and O, in another embodiment from O and S, in another embodiment they are O atoms. In another embodiment, the number of ring heteroatoms in Het is 1. In one embodiment, two ring oxygen atoms in Het are not present at adjacent ring positions, in another embodiment two ring heteroatoms selected from the group consisting of O and S are not present at adjacent ring positions, in another embodiment, two ring heteroatoms are not present at adjacent ring positions. Ring nitrogen atoms in Het carry a hydrogen atom or a substituent as indicated. In one embodiment, optional substituents at ring nitrogen atoms in Het are $(C_1-C_4)$-alkyl substituents. In one embodiment, optional substituents at ring nitrogen atoms and ring carbon atoms in Het are $(C_1-C_4)$-alkyl substituents. In one embodiment, the number of optional substituents on Het is 1, 2, 3, 4 or 5, in another embodiment 1, 2, 3 or 4, in another embodiment 1, 2 or 3, in another embodiment 1 or 2, in another embodiment 1. Het may be attached via any suitable ring carbon atom. In one embodiment, Het is attached via a ring carbon atom which is not adjacent to a ring heteroatom. Het may be 4-membered, 5-membered, 6-membered or 7-membered. In one embodiment, Het is 4-membered or 5-membered, in another embodiment 5-membered to 7-membered, in another embodiment 5-membered or 6-membered, in another embodiment 4-membered. Examples of Het where it is selected from one embodiment are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, [1,3]dioxolanyl including [1,3]dioxolan-2-yl and [1,3]dioxolan-4-yl, [1,4]dioxanyl including [1,4]dioxan-2-yl, thietanyl including thietan-2-yl and thietan-3-yl, tetrahydrothiophenyl including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, [1,4]dithianyl including [1,4]dithian-2-yl, azetidinyl including azetidin-2-yl and azetidin-3-yl, pyrrolidinyl including pyrrolidinyl-2-yl and pyrrolidinyl-3-yl, piperidinyl including piperidinyl-2-yl, piperidinyl-3-yl and piperidinyl-4-yl, azepanyl including azepan-2-yl, azepan-3-yl and azepan-4-yl, oxazolidinyl including oxazolidin-2-yl, oxazolidin-4-yl and oxazolidin-5-yl, thiazolidinyl including thiazolidin-2-yl, thiazolidin-4-yl and thiazolidin-5-yl, morpholinyl including morpholin-2-yl and morpholin-3-yl, thiomorpholinyl including thiomorpholin-2-yl and thiomorpholin-3-yl, all of which are optionally substituted as indicated with respect to Het.

The invention provides all compounds of the formula I wherein one or more structural elements such as groups, substituents and numbers are defined as in any of the specified embodiments or definitions of the elements or have one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratio, and their physiologically acceptable salts, and the physiologically acceptable solvates, are a subject of the present invention.

An example of compounds according to the invention which are defined with respect to any structural elements as in the indicated embodiments of the invention or definitions of such elements and which are part of the subject matter of the invention are compounds of the formula I in any of their stereoisomeric forms or a mixture of stereoisomeric forms in any ratio, and the physiologically acceptable salts thereof, and the physiologically acceptable solvates of such compounds and such salts, in which $R^3$ is selected from the group consisting of $(C_1-C_6)$-alkyl, $(C_3-C_7)$-cycloalkyl-$C_uH_{2u}$— and Het-$C_vH_{2v}$—, in which u and v are selected from the group consisting of 1 and 2, or $R^3$ is a radical of a saturated or unsaturated 3-membered to 10-membered monocyclic or bicyclic ring which contains 0, 1 or 2 identical or different ring heteroatoms selected from the group consisting of N, O and S, where one or two of the ring nitrogen atoms may carry a hydrogen atom or a $(C_1-C_4)$-alkyl substituent and one of the ring sulfur atoms may carry one or two oxo groups and where the radical of a ring is optionally substituted at one or more ring carbon atoms by identical or different substituents $R^{31}$, with the proviso that $R^3$ may not represent $(C_1-C_6)$-alkyl if A represents S;
Het is a radical of a saturated 4-membered to 6-membered monocyclic heterocycle which contains 1 ring heteroatom selected from the group consisting of N, O and S and which is attached via a ring carbon atom, where the radical of a heterocycle is optionally substituted by one or more identical or different substituents selected from the group consisting of fluorine and $(C_1-C_4)$-alkyl;
and all other groups and numbers are defined as in the general definition of the compounds of the formula I or in one of the indicated embodiments of the invention or definitions of structural elements.

Another such example are compounds of the formula I in any of their stereoisomeric forms or in a mixture of stereoisomeric forms in any ratio, and their physiologically acceptable salts, and the physiologically acceptable solvates of such compounds or such salts, in which
A is selected from the group consisting of O and S;
X is selected from the group consisting of $(C_1-C_6)$-alkanediyl, $(C_2-C_6)$-alkenediyl and $(C_1-C_6)$-alkanediyloxy;
Y is a 4-membered to 7-membered saturated monocyclic or bicyclic heterocycle which, in addition to the ring nitrogen atom shown in formula I, contains 0 or 1 ring heteroatoms selected from the group consisting of N, O and S, where the additional ring nitrogen atom may carry a hydrogen atom or a $(C_1-C_4)$-alkyl substituent and the ring sulfur atom may carry one or two oxo groups and where the heterocycle is optionally substituted at one or more ring carbon atoms by identical or different $(C_1-C_4)$-alkyl substituents;
$R^1$ is selected from the group consisting of $(C_1-C_6)$-alkyl, $(C_3-C_7)$-cycloalkyl-$C_tH_{2t}$— and Het-$C_tH_{2t}$—, where t is selected from the group consisting of 0, 1 and 2;
$R^2$ is selected from the group consisting of phenylene and pyridindiyl, where the phenylene and the pyridinediyl are optionally substituted at one or more ring carbon atoms by identical or different substituents $R^{22}$;
$R^3$ is selected from the group consisting of $(C_1-C_6)$-alkyl, $(C_3-C_7)$-cycloalkyl-$C_uH_{2u}$— and Het-$C_vH_{2v}$—, in which u and v are selected from the group consisting of 1 and 2, or $R^3$ is a radical of a saturated or unsaturated 3-membered to 10-membered monocyclic or bicyclic ring which contains 0, 1 or 2 identical or different ring heteroatoms selected from the group consisting of N, O and S, where one or two of the ring nitrogen atoms may carry a hydrogen atom or a $(C_1-C_4)$-alkyl substituent and one of the ring nitrogen atoms may carry one or two oxo groups and where the radical of a ring is optionally substituted at one or more ring nitrogen atoms by identical or different substituents $R^{31}$, with the proviso that $R^3$ may not represent $(C_1-C_6)$-alkyl if A represents S;
Het is a radical of a saturated 4-membered to 6-membered monocyclic heterocycle which contains 1 ring heteroatom selected from the group consisting of N, O and S and which is attached via a ring carbon atom, where the radical of a heterocycle is optionally substituted by one or more identical or different substituents selected from the group consisting of fluorine and $(C_1-C_4)$-alkyl;
and all other groups and numbers are defined as in the general definition of the compounds of the formula I or in one of the indicated embodiments of the invention or definitions of structural elements.

Another such example are compounds of the formula I in any of their stereoisomeric forms or in a mixture of stereoisomeric forms in any ratio, and their physiologically acceptable salts, and the physiologically acceptable solvates of such a compound or such a salt, in which
A is O;
X is selected from the group consisting of $(C_1-C_6)$-alkanediyl and $(C_1-C_6)$-alkanediyloxy;
Y is a 4-membered to 6-membered saturated monocyclic heterocycle which, in addition to the ring nitrogen atom shown in formula I, contains no further ring heteroatoms, where the ring is optionally substituted at one or more ring carbon atoms by identical or different $(C_1-C_4)$-alkyl substituents;
$R^1$ is selected from the group consisting of $(C_1-C_6)$-alkyl and $(C_3-C_7)$-cycloalkyl-$C_tH_{2t}$—, where t is selected from the group consisting of 0 and 1;
$R^2$ is phenylene which is optionally substituted at one or more ring carbon atoms by identical or different substituents $R^{22}$;
$R^3$ is selected from the group consisting of $(C_3-C_7)$-cycloalkyl-$C_uH_{2u}$— and Het-$C_vH_{2v}$—, in which u and v are selected from the group consisting of 1 and 2, or $R^3$ is a radical of a saturated or unsaturated 3-membered to 7-membered monocyclic or bicyclic ring which contains 0, 1 or 2 identical or different ring heteroatoms selected from the group consisting of N, O and S, where one or two of the ring nitrogen atoms may carry a hydrogen atom or a $(C_1-C_4)$-alkyl substituent and one of the ring sulfur atoms may carry one or two oxo groups and where the radical of a ring is optionally substituted at one or more ring carbon atoms by identical or different substituents $R^{31}$, with the proviso that $R^3$ may not represent $(C_1-C_6)$-alkyl if A represents S;
$R^4$ is selected from the group consisting of hydrogen and $(C_1-C_4)$-alkyl;
$R^{22}$ is selected from the group consisting of halogen, hydroxyl, $(C_1-C_4)$-alkyl and $(C_1-C_4)$-alkyloxy;
$R^{31}$ is selected from the group consisting of halogen, $(C_1-C_4)$-alkyl, $(C_3-C_7)$-cycloalkyl, hydroxyl and $(C_1-C_4)$-alkyloxy;
Het is a radical of a saturated 4-membered to 6-membered monocyclic heterocycle which contains 1 ring heteroatom selected from the group consisting of O and S and which is attached via a ring carbon atom, where the radical of a heterocycle is optionally substituted by one or more identical or different substituents selected from the group consisting of fluorine and $(C_1-C_4)$-alkyl;
where all cycloalkyl groups independently of one another and independently of other substituents are optionally substituted by one or more identical or different substituents which are selected from the group consisting of fluorine and $(C_1-C_4)$-alkyl;
where all alkyl, alkanediyl, $C_rH_{2r}$, $C_uH_{2u}$ and $C_vH_{2v}$ groups independently of one another and independently of other substituents are optionally substituted by one or more fluorine substituents.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that they are a subject of the present invention in any of their stereoisomeric forms and or a mixture of stereoisomeric forms in any ratio, and in the form of their physiologically acceptable salts, and in the form of the physiologically acceptable solvates of such compounds or such salts. Irrespective of whether a specific compound is disclosed herein as a free compound and/or as a specific salt, the invention provides the compound both in the form of the free compound and in the form of all its physiologically acceptable salts, and if a specific salt is disclosed, additionally in the form of this specific salt, and in the form of the physiologically acceptable solvates of such a compound or such a salt. Thus, the invention also provides a compound of the formula I which is chosen from one or more of the specific compounds of the formula I disclosed herein, including the example compounds specified below, and the physiologically acceptable salts thereof, and the physiologically acceptable solvates of such a compound or such salts, wherein the invention provides the compound of the formula I in any of its stereoisomeric forms or a mixture of stereoisomeric forms in any ratio, if applicable. An example which may be mentioned is a compound of the formula I or a physiologically acceptable salt thereof or a physiologically acceptable solvate of such a compound or such a salt, selected from the group consisting of
(S)-1-(2-{4-[5-(2,5-difluorophenoxy)-7-propoxyoxazolo[5,4-d]pyrimidin-2-yl]-2,6-dimethylphenoxy}acetyl)pyrrolidine-2-carboxylic acid
(S)-1-(2-{-4-[5-(trans-2-fluorocyclohexyloxy)-7-propoxyoxazolo[5,4-d]pyrimidin-2-yl]-2,6-dimethylphenoxy}acetyl)pyrrolidine-2-carboxylic acid
(S)-1-(2-{4-[5-(2-fluorophenoxy)-7-propoxyoxazolo[5,4-d]pyrimidin-2-yl]-2,6-dimethylphenoxy}acetyl)pyrrolidine-2-carboxylic acid
(S)-1-(2-{4-[5-(5-fluoro-2-methylphenoxy)-7-propoxyoxazolo[5,4-d]pyrimidin-2-yl]-2,6-dimethylphenoxy}acetyl)pyrrolidine-2-carboxylic acid
(S)-1-(2-{4-[(5-(3-fluoro-4-methylphenoxy)-7-propoxyoxazolo[5,4-d]pyrimidin-2-yl]-2,6-dimethylphenoxy}acetyl)pyrrolidine-2-carboxylic acid
(S)-1-(2-{2,6-dimethyl-4-[7-propoxy-5-(pyridin-3-yloxy)oxazolo[5,4-d]pyrimidin-2-yl]phenoxy}acetyl)pyrrolidine-2-carboxylic acid
(S)-1-(2-{4-[5-(2,4-difluorophenoxy)-7-propoxyoxazolo[5,4-d]pyrimidin-2-yl]-2,6-dimethylphenoxy}acetyl)pyrrolidine-2-carboxylic acid
(S)-1-{2-[2,6-dimethyl-4-(5-phenoxy-7-propoxyoxazolo[5,4-d]pyrimidin-2-yl)-phenoxy]acetyl}pyrrolidine-2-carboxylic acid and
(S)-1-(2-{4-[5-(3-chlorophenoxy)-7-propoxyoxazolo[5,4-d]pyrimidin-2-yl]-2,6-dimethylphenoxy}acetyl)pyrrolidine-2-carboxylic acid,
where the trans-2-fluorocyclohexyloxy grouping in the compound (S)-1-(2-{4-[5-(trans-2-fluorocyclohexyloxy)-7-propoxyoxazolo[5,4-d]pyrimidin-2-yl]-2,6-dimethylphenoxy}acetyl)pyrrolidine-2-carboxylic acid may be present in S,S-configuration or R,R-configuration or a mixture of these two forms of the grouping in any ratio.

Another subject of the present invention are processes for the preparation of the compounds of the formula I and their salts and solvates, by which the compounds are obtainable and which are outlined in the following. In one process, a compound of the formula II is reacted with a compound of the formula III to give a compound of the formula I

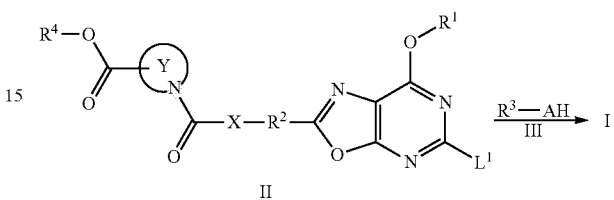

where the groups A, X, Y, $R^1$, $R^2$, $R^3$ and $R^4$ in the compounds of the formulae II and III are defined as in the compounds of the formula I and additionally functional groups can be present in protected form or in the form of a precursor group which is later converted into the final group. The group $L^1$ in the compounds of the formula II is a leaving group which can be replaced in a nucleophilic aromatic substitution reaction, such as a halogen atom, for example chlorine or bromine, or a sulfoxide group or a sulfone group, for example a group of the formula —S(O)-Alk or —S(O)$_2$-Alk where Alk is a $(C_1-C_4)$-alkyl group, for example methyl or ethyl.

The reaction of the compounds of the formulae II and III is a nucleophilic aromatic substitution reaction at the carbon atom in position 5 of the oxazolo[5,4-d]pyrimidine ring, i.e. in the pyrimidine grouping, and can be carried out under standard conditions for such reactions, which are well known to the person skilled in the art. In general, the reaction is, depending on the particular circumstances of the case in question, carried out in an inert solvent, for example a hydrocarbon or a chlorinated hydrocarbon such as benzene, toluene, xylene, chlorobenzene, dichloromethane, chloroform or dichloroethane, an ether such as tetrahydrofuran (THF), dioxane, dibutyl ether, diisopropyl ether or 1,2-dimethoxyethane (DME), a ketone such as acetone or butan-2-one, an ester such as ethyl acetate or butyl acetate, a nitrile such as acetonitrile, an amine such as N,N-dimethylformamide (DMF) or N-methylpyrrolidin-2-one (NMP), or a mixture of solvents, at temperatures of from about 20° C. to about 160° C., for example at temperatures of from about 40° C. to about 100° C. In general, it is favorable to add a base to increase the nucleophilicity of the compound of the formula III, for example a tertiary amine, such as triethylamine, ethyldiisopropylamine or N-methylmorpholine, or an inorganic base such as an alkaline earth metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula II, a compound of the formula III may also separately be treated with a base and converted into a salt.

The starting materials of the formulae II and III can be obtained by processes described in the literature or analogously to processes described in the literature, and in many cases they are commercially available. Compounds of the formula IIa, i.e compounds of the formula II in which $L^1$ is, for example, a sulfoxide group of the formula Alk-S(O)— or a sulfone group of the formula Alk-S(O)$_2$—, can be obtained by reacting an aminomalonic ester of the formula IV with an activated carboxylic acid derivative of the formula V to give a compound of the formula VI, reacting the latter compound with thiourea of the formula VII to give a compound of the formula VIII, alkylating the thiol with an alkylation reagent of the formula IX to give the thioether of the formula X, cyclizing the latter compound with formation of the oxazolo[5,4-d]pyrimidine ring system to give the compound of the formula XI, alkylating the latter compound at the oxygen atom of the keto group or the tautomeric hydroxyl group using an alkylating reagent of the formula XII, introducing the grouping R"O—C(O)—X-into the compound of the formula XIII by reaction with a compound of the formula XIV, deprotecting the resulting compound of the formula XV to give the carboxylic acid of the formula XVI, introducing the grouping R$^4$O—C(O)—Y— by reaction with a compound of the formula XVII and oxidizing the thioether grouping in the resulting compound of the formula XVIII to give the corresponding sulfoxide or sulfone of the formula IIa.

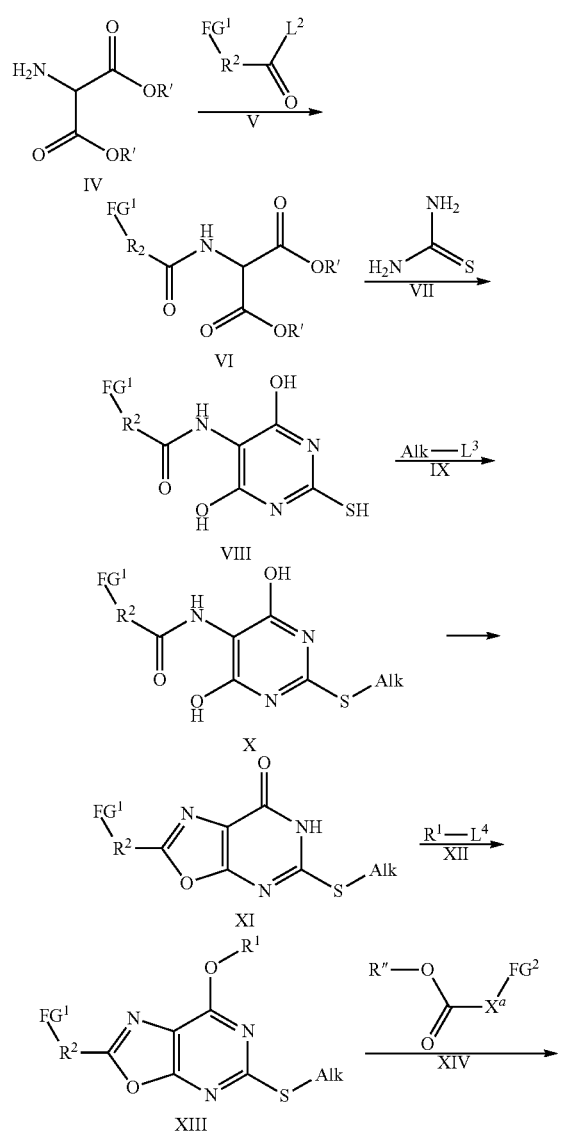

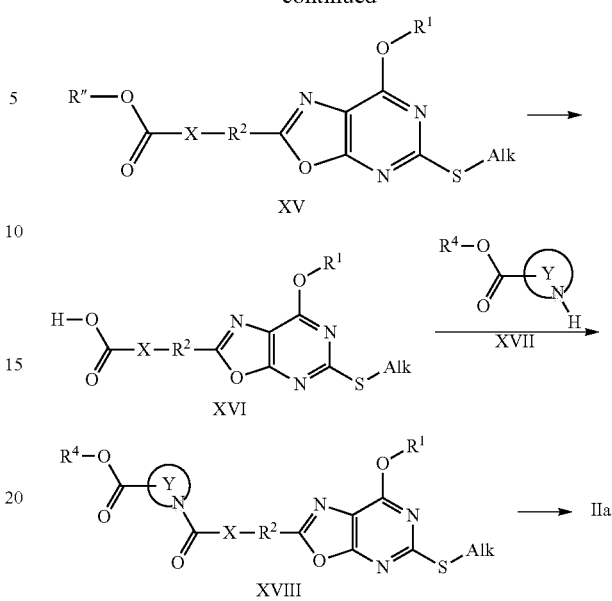

The order in which the structural units are introduced during the synthesis of a compound of the formula I may also be different; for example, in a compound of the formula XV the thioether grouping may initially be oxidized to give the corresponding sulfoxide or sulfone of the formula XIX in which L$^1$ is —S(O)-Alk or —S(O)$_2$-Alk, and the grouping -A-R$^3$ may be introduced by reaction with a compound of the formula III, and the resulting compound of the formula XX may be deprotected giving the carboxylic acid of the formula XXI, and the grouping R$^{40}$—C(O)—Y— may be introduced by reaction with a compound of the formula XVII, giving the compound of the formula I.

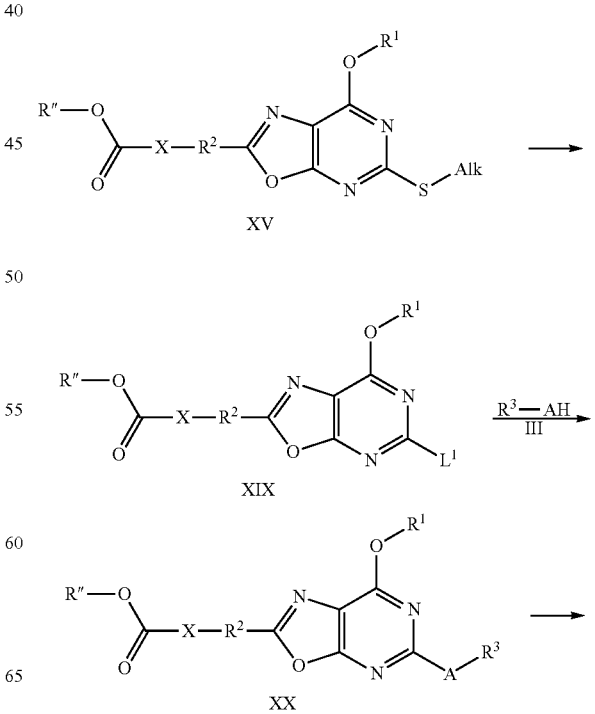

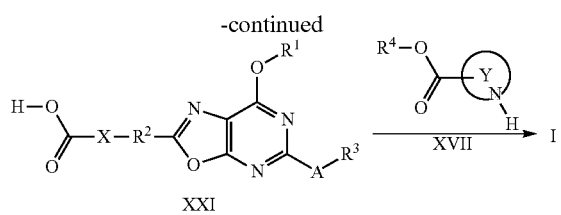

XXI

The groups A, X, Y, $R^1$, $R^2$, $R^3$ and $R^4$ in the compounds of the formulae IIa, V, VI, VIII, X, XI, XII, XIII, XIV, XV, XVI, XVII, XVIII, XIX, XX and XXI are defined as in the compounds of the formula I, and additionally functional groups can be present in protected form or in the form of a precursor group which is later converted into the final group. The group $X^a$ in the compounds of the formula XIV is defined like the group X in the compounds of the formula I or comprises a part of the group X in the desired compound of the formula II, such that after the reaction of the compounds of the formulae XIII and XIV the group $X^a$ and any parts of the groups $FG^1$ and $FG^2$ remaining in the compound of the formula XV together form the desired group X. Thus, for example, if the group X is an alkanediyloxy group, the group $X^a$ in the compound of the formula XIV may be the desired alkanediyloxy group and the group $FG^2$ may be a hydrogen atom attached to the oxygen atom, or the group $X^a$ may be the alkanediyl moiety, the group $FG^2$ is a leaving group and the group $FG^1$ in the compound of the formula XIII is a hydroxyl group whose oxygen atom together with the alkanediyl moiety then, after the alkylation of the compound of the formula XIII with the compound of the formula XIV, forms the desired alkanediyloxy group.

The groups $FG^1$ and $FG^2$ in the compounds of the formulae V, VI, VIII, X, XI, XIII and XIV are functional groups which are suitable for the type of coupling used for the formation of the desired group X from the group $X^a$ and any part of groups $FG^1$ and $FG^2$ remaining in the compound of the formula XV. If, for example, the group $X^a$ is attached via a nucleophilic substitution reaction to the group $R^2$ or to an atom in the group $FG^1$, like an oxygen atom in a hydroxyl group representing $FG^1$, as mentioned above, $FG^2$ may be a leaving group such as a halogen atom such as chlorine, bromine or iodine, or a sulfonyloxy group such as methanesulfonyloxy, trifluoromethanesulfonyloxy or toluenesulfonyloxy. If the group $X^a$ is attached via a transition metal-catalyzed reaction to the group $R^2$, $FG^2$ may be a leaving group such as a boronic acid, boronic ester, dialkylborane or stannane group, and in this case $FG^1$ may be halogen. $FG^2$ may also be a hydrogen atom or a carbon atom which is part of a double bond in an alkenediyl group representing $X^a$, if a Heck reaction is employed to link $X^a$ with $R^2$, and in this case $FG^1$ may be halogen. When a Wittig reaction or a Wittig-Horner reaction is employed to link $X^a$ to $R^2$, $FG^2$ may be a phosphonio group such as triphenylphosphonio or a phosphonyl group such as diethylphosphonyl, and the compound of the formula XIV may be a phosphonium salt or a phosphonic ester, and in this case $FG^1$ may be an aldehyde group —C(O)—H or a ketone group —C(O)-alkyl, and vice versa. In general, the group $FG^1$ is located at the carbon atom in the phenylene group or heterocyclic group which represents $R^2$, which, in the compounds of the formulae XV, IIa and I, carries the group X. The group $FG^1$ in the compounds of the formulae V, VI, VIII, X and XI may also be present in protected form or in the form of a precursor group which is at a later point converted into the group which in the compound of the formula XIII reacts with the compound of the formula XIV. Thus, for example, a hydroxyl group which represents $FG^1$ in the compound of the formula XIII may be present in protected form in the compounds of the formulae V, VI, VIII, X and XI, for example in the form of an etherified hydroxyl group such as a benzyl ether or an alkyl ether such as a methyl ether. Such ethers can be cleaved using methods which are well-known to the person skilled in the art. A summary of methods to remove protective groups can be found in the literature, for example in P. J. Kocienski, Protecting Groups (Thieme Verlag, 1994), or T. W. Greene and P. G. M. Wuts, Protective Groups in Organic Synthesis (John Wiley & Sons, 1999).

The group $L^1$ in the compounds of the formulae IIa and XIX is as defined above. The group $L^2$ in the compounds of the formula V is a nucleophilically substitutable leaving group and may in particular be a halogen atom, such as chlorine or bromine, and the compound of the formula V may thus be a carbonyl halide. $L^2$ may also be a group of the formula $R^2$—C(O)—O, and the compound of the formula V may thus be a carboxylic anhydride, for example. The groups $L^3$ and $L^4$ are leaving groups which can be replaced in a nucleophilic substitution reaction and may be in particular a halogen atom such as chlorine, bromine or iodine, or a sulfonyloxy group such as methanesulfonyloxy, trifluoromethanesulfonyloxy or toluenesulfonyloxy, i.e. the compounds of the formulae IX and XII may be organic halides or sulfonates, for example. The group R' in the compounds of the formulae IV and VI may be alkyl such as, for example, ($C_1$-$C_3$)-alkyl, such as methyl or ethyl. The group R" in the compounds of the formulae XIV, XV, XIX and XX is a group which is suitable for protecting the carboxylic acid function as an ester, for example a ($C_1$-$C_4$)-alkyl group such as methyl, ethyl or tert-butyl or a benzyl group. As mentioned, the compounds of the formula XI can also be present in another tautomeric form, for example in the form of the respective 7-hydroxyoxazolo[5,4-d]pyrimidine derivatives in which the mobile hydrogen atom, which in formula XI is attached to the ring nitrogen atom in the 6-position of the oxazolopyrimidine ring system, is attached to the oxygen atom bonded to the ring carbon atom in position 7. If applicable, it applies to all compounds involved in the preparation of the compounds of the formula I that they may be present in a tautomeric form different from that shown in their formulae. In the reactions of this process for preparing the compounds of the formula II, as in all other reactions carried out in the preparation of the compounds of the formula I, starting matrials may also be employed in the form of a salt and/or products may be obtained in the form of a salt. Thus, for example, compounds of the formula IV may be employed in the form of an acid addition salt such as the hydrochloride.

The reaction of the compounds of the formulae IV and V can be carried out under standard conditions for the acylation of an amine with an activated carboxylic acid derivative such as an acid halide or anhydride. In general, the reaction is carried out in an inert solvent, for example a hydrocarbon or a chlorinated hydrocarbon such as benzene, toluene, xylene, chlorobenzene, dichloromethan, chloroform or dichloroethane, an ether such as THF, dioxane, dibutyl ether, diisopropyl ether or DME, a ketone such as acetone or butan-2-one, an ester such as ethyl acetate or butyl acetate, or water, or a mixture of solvents, at temperatures of from about –10° C. to about 40° C., for example at temperatures of from about 0° C. to about 30° C. In general, the reaction is carried out with addition of a base, for example a tertiary amine, such as triethylamine, ethyldiisopropylamine or N-methylmorpholine or an inorganic base such as, an alkali metal hydroxide, carbonate or bicarbonate such as sodium hydroxide, potassium hydroxide, sodium carbonate, potassium carbonate or sodium bicarbonate. The reaction of the compounds of the formulae VI and VII is generally carried out in an inert solvent, for example an alcohol such as methanol, ethanol or isopropanol, or an ether such as THF, dioxane or DME, or a mixture of solvents, at temperatures of from about 20° C. to about 80° C., for example temperatures of about 40° C. to about 80° C., in the presence of a base, for example an alkoxide such as sodium methoxide, sodium ethoxide, potassium methoxide or potassium tert-butoxide.

The reaction of the compounds of the formulae VIII and IX is a nucleophilic substitution reaction at the carbon atom in the group Alk, which carries the group $L^3$, and can be carried out under standard conditions for such reactions, which are well-known to the person skilled in the art. In general, the reaction is, depending on the particular circumstances of the case in question, carried out in an inert solvent, for example a hydrocarbon or a chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such as acetonitrile, an amide such as DMF or NMP, or a mixture of solvents including two-phase mixtures with aqueous solutions, at temperatures of from about −20° C. to about 100° C., for example at temperatures of from about −10° C. to about 30° C. In general, it is favorable to add a base to increase the nucleophilicity of the compound of the formula VII and/or to bind an acid released during the reaction, for example a tertiary amine, such as triethylamine, ethyldiisopropylamine or N-methylmorpholine, or an inorganic base such as an alkali metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula IX, a compound of the formula VIII may also separately be treated with a base and converted into a salt.

The cyclization of the compound of the formula X to the compound of the formula XI can favorably be carried out in the presence of a phosphorus halide such as phosphorus pentachloride or phosphorus oxychloride or a mixture thereof, in an inert solvent, for example a hydrocarbon or a chlorinated hydrocarbon such as benzene, toluene, xylene, chlorobenzene, dichloromethane, chloroform or dichloroethane, at temperatures of from about 20° C. to about 100° C., for example at temperatures of from about 50° C. to about 80° C.

The reaction of the compounds of the formulae XI and XII is a further nucleophilic substitution reaction at the carbon atom in the group $R^1$, which carries the group $L^4$, and can be carried out under standard conditions for such reactions, which are well-known to the person skilled in the art. In general, the reaction is, depending on the particular circumstances of the case in question, carried out in an inert solvent, for example a hydrocarbon or a chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such as acetonitrile, an amide such as DMF or NMP, or a mixture of solvents, at temperatures of from about 20° C. to about 100° C., for example at temperatures of from about 40° C. to about 80° C. In general, it is favorable to add a base to increase the nucleophilicity of the compound of the formula XI and/or to bind an acid released during the reaction, for example a tertiary amine, such as triethylamine, ethyldiisopropylamine or N-methylmorpholine, or an inorganic base such as an alkali metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula XII, a compound of the formula XI may also separately be treated with a base and converted into a salt. A compound of the formula XI may not only be prepared by reaction with a compound of the formula XII, but can also be converted by reaction with the respective alcohol of the formula $R^1$—OH in which $R^1$ is as defined in the compounds of the formula I and functional groups may additionally be present in protected form or in the form of a precursor group, under the conditions of the Mitsunobu reaction in the presence of an azodicarboxylate such as diethyl azodicarboxylate or diisopropyl azodicarboxylate and a phosphine such as triphenylphosphine or tributylphosphine in an inert aprotic solvent, for example an ether such as THF or dioxane, into a compound of the formula XIII (see O. Mitsunobu, Synthesis (1981), 1-28).

The coupling of compounds of the formula XIII with compounds of the formula XIV can be carried out using reactions of various types, as already mentioned above, for example via an alkylation reaction. Thus, the group $R^2$ can, for example when it carries a hydroxyl group which represents $FG^1$, be alkylated using a compound of the formula XIV in which $FG^2$ is a leaving group suitable for nucleophilic substitution reactions such as a halogen atom such as chlorine, bromine or iodine, or a sulfonyloxy group such as methanesulfonyloxy or toluenesulfonyloxy. The nucleophilic substitution reaction at the carbon atom of the group XIV which carries the group $FG^2$ can be carried out under standard conditions for such reactions, which are well-known to the person skilled in the art. In general, the reaction is, depending on the particular circumstances of the case in question, carried out in an inert solvent, for example a hydrocarbon or a chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such as acetonitrile, an amide such as N,N-dimethylformamide or N-methylpyrrolidin-2-one, or a mixture of solvents, at temperatures of from about 20° C. to about 100° C., for example at temperatures of from about 40° C. to about 80° C. In general, it is favorable to add a base to increase the nucleophilicity of the compound of the formula XIII and/or to bind an acid released during the reaction, for example a base, for example a tertiary amine, such as triethylamine, ethyldiisopropylamine or N-methylmorpholine, or an inorganic base such as an alkali metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula XIV, a compound of the formula XIII in which $FG^1$ is hydroxyl may also separately be treated with a base and converted into a salt. A compound of the formula XIV in which $FG^1$ is hydroxyl can be converted into a compound of the formula XV not only by reaction with a compound of the formula XIV in which $FG^2$ is a leaving group, as indicated, but also by reaction with the corresponding alcohol, i.e. with a compound of the formula XIV in which $FG^1$ is hydroxyl, under the conditions of the Mitsunobu reaction indicated above. The coupling of compounds of the formula XIII with compounds of the formula XIV via a transition metal-catalyzed reaction can also be carried out under the conditions of palladium-catalyzed crosscoupling reactions such as the Heck, Stille or Suzuki coupling reaction (see A. de Meijere and F. Diederich (Ed.), Metal-Catalyzed Cross-Coupling Reactions (Wiley-VCH, 2004)).

The deprotection of the R"-protected carboxylic acid group in the compounds of the formula XV to give the compounds of the formula XVI can be achieved by standard methods which are well known to a person skilled in the art and are summarized in the above-mentioned books by P. J. Kocienski and by T. W. Greene and P. G. M. Wuts, for example under basic conditions by treatment with an alkali metal hydroxide such as sodium hydroxide or lithium hydroxide in the case of compounds in which R" is an alkyl group such as methyl or ethyl, by treatment with trifluoroacetic acid in the case of compounds in which R" is a tert-butyl group, or by hydrogenation in the presence of a transition metal catalyst such as palladium on charcoal in the case of compounds in which R" is a benzyl group.

For the introduction of the moiety $R^4O$—C(O)—Y—, the carboxylic acid group HO—C(O)—in the compounds of the formula XVI is generally activated in situ by means of a customary amide coupling reagent or converted into a reactive carboxylic acid derivative which can be prepared in situ or isolated. For example, the compound of the formula XVI can be converted into an acid halide by treatment with thionyl chloride, phosphorus pentachloride, phosphorus tribromide or oxalyl chloride, or treated with an alkyl chloroformate like ethyl chloroformate or isobutyl chloroformate to give a mixed anhydride. Customary coupling reagents which can be employed, are propanephosphonic anhydride, N,N'-carbonyldiazoles like N,N'-carbonyldiimidazole (CDI), carbodiimides like 1,3-diisopropylcarbodiimide (DIC), 1,3-dicyclohexylcarbodiimide (DCC) or 1-(3-dimethylaminopropyl)-3-ethylcarbodiimide hydrochloride (EDC), carbodiimides together with additives like 1-hydroxy-benzotriazole (HOBT) or 1-hydroxy-7-azabenzotriazole (HOAT), uronium-based coupling reagents like O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetrannethyluronium tetrafluoroborate (TOTU), and phosphonium-based coupling agents like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromotripyrrolidinophosphonium hexafluorophosphate (PyBroP).

The reaction conditions for the preparation of the compound of the formula XVIII from compounds of the formulae XVI and XVII depend on the particular circumstances of the case in question, for example the coupling reagent used, and are well known to the person skilled in the art. Thus, for example, in the case of the activation of the compound of the formula XVI via an acid chloride or acid bromide, the coupling reaction with the cyclic amine of the formula XVII is generally carried out in an inert solvent, for example a hydrocarbon or chlorinated hydrocarbon or an ether like those listed above, an ester such as ethyl acetate or butyl acetate, a nitrile such as acetonitrile, or water, or a mixture of solvents including a mixture of water and an organic solvent miscible or not miscible with water, at temperatures of from about −10° C. to about 100° C., in particular at temperatures of from about 0° C. to about 80° C., for example at about room temperature. Expediently, the reaction of an acyl halide derived from the carboxylic acid of the formula XVI with a compound of the formula XVII is carried out in the presence of a base such as a tertiary amine such as triethylamine, ethyldiisopropylamine, N-methylmorpholine or pyridine, or an inorganic base such as an alkali metal hydroxide, carbonate or bicarbonate, for example sodium hydroxide, potassium hydroxide, sodium carbonate or sodium bicarbonate. In the case of the activation of the carboxylic acid group in the compounds of the formula XVI with the aid of an amide coupling agent such as, for example, a carbodiimide or TOTU, the reaction is generally carried out under anhydrous conditions in an inert aprotic solvent, for example an ether such as THF, dioxane or DME or an amide such as DMF or NMP, at temperatures of from about −10° C. to about 80° C., in particular at temperatures of from about 0° C. to about 60° C. in the presence of a base such as a tertiary amine such as triethylamine, ethyldiisopropylamine or N-methylmorpholine. If the compound of the formula XVII is employed in the form of an acid addition salt for the reaction with the compound of the formula XVI, in general an amount of a base sufficient for releasing the free compound of the formula XVII is added.

The oxidation of the Alk-S group in the compounds of the formula XVIII to the sulfoxide or sulfone group in the compounds of the formula IIa can be carried out with the aid of hydrogen peroxide or a peracid such as 3-chloroperbenzoic acid or monoperoxyphthalic acid in an inert solvent, for example a chlorinated hydrocarbon such as dichloromethane or chloroform or an ester such as ethyl acetate or butyl acetate, at temperatures of from about 0° C. to about 40° C., for example at about 20° C.

The above explanations of the oxidation of the compounds of the formula XVIII to the compounds of the formula IIa apply correspondingly to the oxidation of the compounds of the formula XV to the compounds of the formula XIX, and likewise the explanations given for the reaction of the compounds of the formulae II and III, the deprotection of the carboxylic acid group in the compounds of the formula XV and the reaction of the compounds of the formulae XVI and XVII apply correspondingly to the reaction of the compounds of the formulae XIX and III, the deprotection of the carboxylic acid group in the compounds of the formula XX and the reaction of the compounds of the formulae XXI and XVII.

The order of the steps in the preparation of the compounds of the formula X can also be changed, and an aminomalonic ester of the formula IV such as the diethyl ester may initially be reacted in the presence of an alkali metal alkoxide such as sodium ethoxide with thiourea, the sulfur atom may then by alkylated, for example methylated with iodomethane, and the resulting product may be acylated with a compound of the formula V (see M. H. Holschbach et al., Eur. J. Med. Chem. 41 (2006), 7-15).

Further compounds of the formula I can be obtained from suitable compounds prepared according to the above-described processes by functionalization or modification of any functional groups present according to standard procedures, for example by esterification, amidation, hydrolysis, etherification, alkylation, acylation, sulfonylation, reduction, oxidation, conversion into salts, and others. For example, a hydroxyl group, which may be liberated from an ether group by ether cleavage, for example by means of boron tribromide, or from a protected hydroxyl group by deprotection, can be esterified to give a carboxylic acid ester or a sulfonic acid ester, or etherified. Etherifications of hydroxyl groups can favorably be performed by alkylation with the respective halogen compound, for example a bromide or iodide, in the presence of a base, for example an alkali metal carbonate such as potassium carbonate or cesium carbonate, in an inert solvent, for example an amide like DMF or NMP or a ketone like acetone or butan-2-one, or with the respective alcohol under the conditions of the Mitsunobu reaction referred to above. A hydroxyl group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with an activated carboxylic acid which may be obtained from the carboxylic acid by treatment with a coupling agent such as CDI, a carbodiimide such as DCC or EDC, HATU, TOTU, TBTU, for example. A carboxylic ester group can be hydrolyzed under acidic or basic conditions to give a carboxylic acid. A carboxylic acid group can be activated or converted into a reactive derivative as mentioned above and reacted with an alcohol or an amine or ammonia to give an ester or amide. A primary amide can be dehydrated to give a nitrile. A sulfur atom, for example in an alkyl-S group or in a heterocyclic ring, can be oxidized with a peroxide like hydrogen peroxide or a peracid to give a sulfoxide moiety S(O) or a sulfone moiety $S(O)_2$. A carboxylic acid group, a carboxylic acid ester group and a ketone group can be reduced to an alcohol, for example by means of a complex hydride such as lithium aluminum hydride, lithium borohydride or sodium borohydride. A compound of the formula I or an intermediate such as a compound of the formula II, which contains a double bond or a triple bond in the group X, which can be readily obtained via a transition metal-catalyzed coupling reaction from a compound of the formula XIV containing a double or triple bond in the group $X^a$ and a compound of the formula XIII according to the description above, can be converted by hydrogenation in the presence of hydrogenation catalyst such as a palladium catalyst into a compound in which X is a saturated group.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed in the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protective groups amino-protective groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protective groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group, which can be converted into an amino group by reduction, for example by catalytic hydrogenation, may be mentioned. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae II, IIa, III, IV, V, VI, VIII, X, XI, XII, XIII, XIV, XV, XVI, XVII, XVIII, XIX, XX and XXI, in which A, X, $X^a$, Y, $R^1$, $R^2$, $R^3$, $R^4$, R', Alk, $FG^1$, $FG^2$, $L^1$, $L^2$ and $L^4$ are defined as above, in any of their stereoisomeric forms or a mixture of stereoisomeric forms in any ratio, and their salts, and solvates of such compounds or such salts, and their use as intermediates. The invention also includes all tautomeric forms of said intermediates and starting compounds. All explanations given above and embodiments specified above with respect to the compounds of the formula I also apply correspondingly to said intermediates and starting materials. Subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of such compounds or such salts.

The compounds of the formula I, optionally in combination with other pharmacologically active compounds, can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions. The compounds of the formula I can additionally be used in modes of local drug delivery, for example in coated stents for preventing or reducing in-stent restenosis or by applying them locally by means of a catheter. The appropriate administration form depends, among others, on the disease to be treated and on its severity.

The amount of a compound of the formula I and/or its physiologically acceptable salts and/or solvates present in the pharmaceutical compositions normally ranges from about 0.2 to about 800 mg, for example from about 0.5 to about 500 mg, for example from about 1 to about 200 mg, per unit dose, but depending on the type of the pharmaceutical composition it may also be higher. The pharmaceutical compositions usually comprise from about 0.5 to about 90 percent by weight of the compound of the formula I and/or its physiologically acceptable salts and/or solvates. The production of the pharmaceutical compositions can be carried out in a manner known per se. To this end, one or more compounds of the formula I and/or their physiologically acceptable salts and/or solvates together with one or more solid or liquid pharmaceutical carrier substances, or vehicles, and/or additives, or auxiliary substances, and, if a combination medicament is desired, other pharmacologically active compounds having therapeutic or prophylactic action are brought into a suitable form for administration and dosage which can be used in human or veterinary medicine. As carrier substances and additives, suitable organic and inorganic substances can be used which do not react in an undesired manner with the compounds of the formula I or their physiologically acceptable salts or solvates. As examples of types of additives which can be contained in the pharmaceutical compositions and medicaments, lubricants, preservatives, thickeners, stabilizers, disintegrants; wetting agents, agents for achieving a depot effect, emulsifiers, salts, for example for influencing the osmotic pressure, buffer substances, colorants, flavorings and aromatic substances may be mentioned. Examples of carrier substances and additives are water, physiological sodium chloride solution, vegetable oils, waxes, alcohols such as ethanol, isopropanol, 1,2-propanediol, benzyl alcohols or glycerol, polyols, mannitol, polyethylene glycols, polypropylene glycols, glycerol triacetate, polyvinylpyrrolidone, gelatin, cellulose, carbohydrates such as lactose, glucose, saccharose or starch like corn starch, stearic acid and its salts such as magnesium stearate, talc, lanolin, petroleum jelly, or mixtures thereof, for example mixtures of water with one or more organic solvents such as mixtures of water with alcohols. The compounds of the formula I and their physiologically acceptable salts and solvates can also be lyophilized and the obtained lyophilisates used for the production of injectable compositions, for example.

The dosage of a compound of the formula I and/or a physiologically acceptable salt and/or solvate thereof to be administered depends on the specific case and, as is usual, has to be adapted by the physician according to the customary rules and procedures to the individual circumstances in order to achieve an optimum effect. It depends, for example, on the nature and the severity of the disorder to be treated, the sex, age, weight and individual responsiveness of the human or animal patient, on the efficacy and duration of action of the compound used, on whether the treatment is for the therapy of an acute or chronic disease or prophylactic, or on whether other active ingredients are administered in addition to a compound of the formula I. In general, a daily dose from about 0.01 mg/kg to about 100 mg/kg, or from about 0.1 mg/kg to about 10 mg/kg, or from about 0.3 mg/kg to about 5 mg/kg (in each case mg per kg of bodyweight), for example, is appropriate for administration to an adult weighing about 75 kg in order to obtain the desired results. The daily dose can be administered in a single dose or, in particular when larger amounts are administered, divided into several, for example two, three or four, individual doses. The administration can also be carried out continuously, for example by continuous infusion or injection. Depending on the individual behavior in a specific case, it may be necessary to deviate upward or downward from the indicated dosages.

The examples below illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such trifluoroacetic acid present is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; br=broad) of the signals is given. In the MS characterization, in general the mass number (m/z) of the peak of the molecular ion M, e.g. M+, or of a related ion such as the ion M+1, e.g. [M+1]+, i.e. the protonated molecular ion [M+H]+, which was formed depending on the ionization method used, is given. Generally, the ionization method was electrospray ionization (ESI). The LC/MS conditions used were as follows.

Method LC1

Column: UPLC BEH C18, 50×2.1 mm, 1.7 μm; flow rate: 0.9 ml/min; eluent A: acetonitrile+0.08% formic acid; eluent B: water+0.1% formic acid; gradient: from 5% A+95% B to 95% A+5% B in 1.1 min, then from 95% B to 95% A+5% B over a period of 0.6 min; MS ionization method: ESI⁺

Method LC2

Column: UPLC BEH C18, 50×2.1 mm, 1.7 μm; flow rate: 0.9 ml/min; eluent A: acetonitrile+0.035% formic acid; eluent B: water+0.05% formic acid; gradient: from 5% A+95% B to 95% A+5% B in 1.1 min, then 95% A+5% B for 0.6 min; MS ionization method: ESI⁺

Method LC3

Column: Phenomenex Mercury MS Luna 3 μm C18(2) 100 Angstrom, 10×2.0 mm; flow rate 1.1 ml/min; eluent A: acetonitrile; eluent B: water+0.05% TFA; gradient: from 20% A+80% B to 95% A+5% B in 0.8 min, then 95% A+5% B for 0.6 min; then 20% A+80% B in 0.05 min; MS ionization method: ESI+

EXAMPLE 1

(S)-1-(2-{4-[5-(2,5-Difluorophenoxy)-7-propoxyoxazolo[5,4-d]pyrimidin-2-yl]-2,6-dimethylphenoxy}acetyl)pyrrolidine-2-carboxylic acid

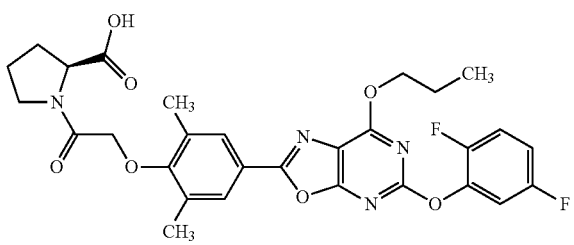 [SMILES: CCCOc1nc(Oc2cc(F)ccc2F)nc2oc(-c3cc(C)c(OCC(=O)N4CCC[C@H]4C(=O)O)c(C)c3)nc12]

(a) Diethyl 2-(4-methoxy-3,5-dimethylbenzoylamino)malonate 116.8 g of diethyl aminomalonate hydrochloride were dissolved in 700 ml of dichloromethane, and 231 ml of triethylamine were added with cooling in an ice bath. A solution of 109.6 g of 4-methoxy-3,5-dimethylbenzoyl chloride in 400 ml of dichloromethane was then slowly added dropwise. After 2 h at 0° C., 200 ml of water were added slowly. After phase separation, the aqueous phase was extracted twice with 200 ml of dichloromethane. The combined organic phases were washed with 2M hydrochloric acid and then with water, dried with sodium sulfate, filtered and evaporated. The residue was treated with methyl tert-butyl ether, after which the precipitate obtained was filtered off, which gave 178.7 g of the title compound.

(b) Sodium 4,6-dihydroxy-5-(4-methoxy-3,5-dimethylbenzoylamino)pyrimidine-2-thiolate 1.5 equivalents of sdoium methoxide (30% strength solution in methanol) were added to 20.6 g of thiourea in 900 ml of absolute ethanol. After addition of 91 g of diethyl 2-(4-methoxy-3,5-dimethylbenzoylamino)malonate in small portions, the mixture was stirred at 60° C. for 3 h. The mixture was then cooled to room temperature and the precipitate was filtered off with suction, washed with 100 ml of ethanol and 100 ml of diethyl ether and dried under reduced pressure. This gave 78.2 g of the crude title compound.

(c) N-(4,6-Dihydroxy-2-methylsulfanylpyrimidin-5-yl)-4-methoxy-3,5-dimethylbenzamide 19.1 g of sodium 4,6-dihydroxy-5-(4-methoxy-3,5-dimethylbenzoylamino)pyrimidine-2-thiolate in 190 ml of water and 80 ml of N-methylpyrrolidin-2-one were cooled to 0° C. With cooling, 5.9 g of sodium hydroxide were added, after which the mixture was stirred at 0° C. for 30 min. A solution of 3.7 ml of iodomethane in 4.3 ml of N-methylpyrrolidin-2-one was then added. After the reaction had ended (2 h), the mixture was acidified with concentrated hydrochloric acid. The precipitate obtained was filtered off with suction, washed with water and dried under reduced pressure. This gave 10.1 g of the title compound.
LC/MS (Method LC1): Rt=1.03 min; m/z=336.1 [M+H]$^+$ (d) 2-(4-Methoxy-3,5-dimethylphenyl)-5-methylsulfanyloxazolo[5,4-d]pyrimidin-7-ol 10.1 g of N-(4,6-dihydroxy-2-methylsulfanylpyrimidin-5-yl)-4-methoxy-3,5-dimethylbenzamide in 55 ml of phosphorus oxychloride were heated at 60° C. for 3 h. After cooling, the solid obtained was filtered off with suction and washed with methyl tert-butyl ether. The solid was then dissolved in a mixture of dichloromethane and tetrahydrofuran, washed with saturated aqueous sodium bicarbonate solution, dried and concentrated under reduced pressure. This gave 5.9 g of the title compound. LC/MS (Method LC1): Rt=1.24 min; m/z=318.08 [M+H]$^+$ (e) 2-(4-Methoxy-3,5-dimethylphenyl)-5-methylsulfanyl-7-propoxyoxazolo[5,4-d]pyrimidine 5.9 g of 2-(4-methoxy-3,5-dimethylphenyl)-5-methylsulfanyloxazolo[5,4-d]pyrimidin-7-ol were dissolved in 150 ml of N,N-dimethylformamide, and 7.7 g of potassium carbonate and then 2.7 g of 1-bromopropane were added. The solution was stirred at 60° C. for 5 h and then, after cooling, poured into 150 ml of water. The precipitate was filtered off with suction. The regioisomer mixture obtained was purified by silica gel chromatography (50 g silicon dioxide solute cartridge, heptane/ethyl acetate 9/1). In addition to 1.4 g of 2-(4-methoxy-3,5-dimethylphenyl)-5-methylsulfanyl-6-propyl-6H-oxazolo[5,4-d]pyrimidin-7-one (LC/MS (Method LC1): Rt=1.43 min; m/z=360.13 [M+H]$^+$), 2.5 g of the title compound were obtained.
LC/MS (Method LC1): Rt=1.51 min; m/z=360.13 [M+H]$^+$ (f) 2,6-Dimethyl-4-(5-methylsulfanyl-7-propoxyoxazolo[5,4-d]pyrimidin-2-yl)phenol At −20° C., 0.70 ml of boron tribromide was added slowly to a solution of 2.5 g of 2-(4-methoxy-3,5-dimethylphenyl)-5-methylsulfanyl-7-propoxyoxazolo[5,4-d]pyrimidine in 50 ml of dichloromethane. After 1 h at −20° C. and 2 h at room temperature, the mixture was quenched by addition of saturated aqueous sodium bicarbonate solution, with the temperature being kept below 5° C. After phase separation, the aqueous phase was extracted twice with dichloromethane. The combined organic phases were dried and concentrated under reduced pressure. This gave 2.0 g of the title compound.
LC/MS (Method LC1): Rt=1.41 min; m/z=346.11 [M+H]$^+$ (g) tert-Butyl [2,6-dimethyl-4-(5-methylsulfanyl-7-propoxyoxazolo[5,4-d]pyrimidin-2-yl)-phenoxy]acetate 3.20 g of potassium carbonate and then 0.93 ml of tert-butyl bromoacetate were added to a solution of 2.00 g of 2,6-dimethyl-4-(5-methylsulfanyl-7-propoxyoxazolo[5,4-d]pyrimidin-2-yl)phenol in 20 ml of N,N-dimethylformamide. The mixture was reacted at 60° C. for 1 h and then allowed to cool and poured into water. The precipitate obtained was filtered off with suction and dried under reduced pressure. This gave 2.45 g of the title compound.
LC/MS (Method LC1): Rt=1.52 min; m/z=460.18 [M+H]$^+$ (h) tert-Butyl [4-(5-methanesulfonyl-7-propoxyoxazolo[5,4-d]pyrimidin-2-yl)-2,6-dimethylphenoxy]acetate 250 mg of tert-butyl [2,6-dimethyl-4-(5-methylsulfanyl-7-propoxyoxazolo[5,4-d]pyrimidin-2-yl)phenoxy]acetate were dissolved in 5 ml of dichloromethane. At 0° C., 268 mg of 3-chlorperbenzoic acid were then added, after which the mixture was stirred at room temperature for 12 h. The mixture was treated with 1 M aqueous sodium hydroxide solution, the layers were then separated and the organic layer was subsequently extracted twice with dichloromethane. The combined organic phases were washed with 10% strength aqueous sodium bisulfite solution, dried over sodium sulfate, filtered and evaporated under reduced pressure. This gave 268 mg of the title compound.
LC/MS (Method LC1): Rt=1.38 min; m/z=492.17 [M+H]$^+$ (i) tert-Butyl {4-[5-(2,5-difluorophenoxy)-7-propoxyoxazolo[5,4-d]pyrimidin-2-yl]-2,6-dimethylphenoxy}acetate 62 mg of potassium carbonate and 32 mg of 2,5-difluorophenol were added to a solution of 100 mg of tert-butyl [4-(5-methanesulfonyl-7-propoxyoxazolo[5,4-d]pyrimidin-2-yl)-2,6-dimethylphenoxy]acetate in 1.5 ml of N,N-dimethylformamide. The mixture was stirred at room temperature for 12 h. The mixture was then poured into water, neutralized by addition of 10% strength aqueous sodium bisulfate solution and extracted twice with ethyl acetate. The combined organic layers were dried and concentrated under reduced pressure. After filtration, the solvent was distilled off under reduced pressure and the residue was purified by preparative HPLC, giving 69 mg of the title compound.
LC/MS (Method LC1): Rt=1.47 min; m/z=542.20 [M+H]$^+$

(j) {4-[(5-(2,5-Difluorophenoxy)-7-propoxyoxazolo[5,4-d]pyrimidin-2-yl]-2,6-dimethylphenoxy}acetic acid 69 mg of tert-butyl {4-[5-(2,5-difluorophenoxy)-7-propoxyoxazolo[5,4-d]pyrimidin-2-yl]-2,6-dimethylphenoxy}acetate were dissolved in 1.6 ml of dichloromethane, and 0.8 ml of trifluoroacetic acid was added. After 16 h, the mixture was concentrated and freeze-dried. This gave 71 mg of the title compound.
LC/MS (Method LC1): Rt=1.35 min; m/z=486.33 [M+H]$^+$

(k) tert-Butyl(S)-1-(2-{4-[5-(2,5-difluorophenoxy)-7-propoxyoxazolo[5,4-d]pyrimidin-2-yl]-2,6-dimethylphenoxy}acetyl)pyrrolidine-2-carboxylate 60 mg of {4-[5-(2,5-difluorophenoxy)-7-propoxyoxazolo[5,4-d]pyrimidin-2-yl]-2,6-dimethylphenoxy}acetic acid were dissolved in 1 ml of N,N-dimethylformamide, and 35 mg of 1-ethyl-3-(3-dimethylaminopropyl)carbodiimide hydrochloride, 7 mg of 1-hydroxy-7-azabenzotriazole and 139 µl of N,N-diisopropylethylamine were added, and 5 min later 17 mg of tert-butyl L-prolinate were added. After 16 h at room temperature, 10 ml of water were added, after which the mixture was adjusted to pH 3 by addition of 2 M aqueous hydrochloric acid and extracted twice with ethyl acetate. The combined organic layers were washed with saturated sodium bicarbonate solution and sodium chloride solution, dried and concentrated under reduced pressure. This gave 61 mg of the title compound.
LC/MS (Method LC1): Rt=1.46 min; m/z=639.26 [M+H]$^+$

(l) (S)-1-(2-{4-[5-(2,5-difluorophenoxy)-7-propoxyoxazolo[5,4-d]pyrimidin-2-yl]-2,6-dimethylphenoxy}acetyl)pyrrolidine-2-carboxylic acid 59 mg of tert-butyl(S)-1-(2-{4-[5-(2,5-difluorophenoxy)-7-propoxyoxazolo[5,4-d]pyrimidin-2-yl]-2,6-dimethylphenoxy}acetyl)pyrrolidine-2-carboxylate were dissolved in 1.2 ml of dichloromethane, and 0.5 ml of trifluoroacetic acid was added. After 16 h at room temperature, the mixture was concentrated under reduced pressure and freeze-dried. This gave 53 mg of the title compound.
LC/MS (Method LC1): Rt=1.36 min; m/z=583.19 [M+H]$^+$

Example 2

(S)-1-(2-{4-[5-(trans-2-fluorocyclohexyloxy)-7-propoxyoxazolo[5,4-d]pyrimidin-2-yl]-2,6-dimethylphenoxy}acetyl)pyrrolidine-2-carboxylic acid

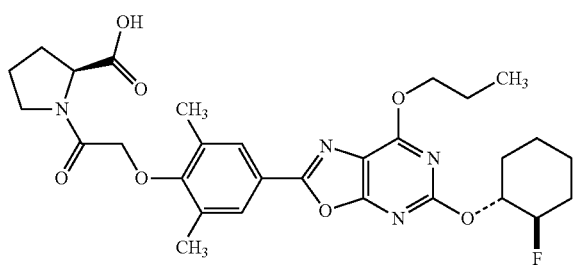

(a) tert-Butyl {4-[5-(trans-2-fluorocyclohexyloxy)-7-propoxyoxazolo[5,4-d]pyrimidin-2-yl]-2,6-dimethylphenoxy}acetate Under an atmosphere of argon and at 0 C, 26 mg of trans-2-fluorocyclohexanol were added to a suspension of 10 mg of sodium hydride (60% in mineral oil) in 2 ml of N,N-dimethylformamide. After 15 min, a solution of 100 mg of tert-butyl [4-(5-methanesulfonyl-7-propoxyoxazolo[5,4-d]pyrimidin-2-yl)-2,6-dimethylphenoxy]acetate in 1 ml of N,N-dimethylformamide was slowly added. After 12 h at room temperature, the mixture was quenched by addition of water and extracted twice with ethyl acetate. The combined organic layers were dried and concentrated under reduced pressure. This gave 101 mg of the title compound.
LC/MS (Method LC1): Rt=1.49 min, m/z=530.26 [M+H]$^+$ and 552.26 [M+Na]$^+$

(b) {4-[5-(trans-2-Fluorocyclohexyloxy)-7-propoxyoxazolo[5,4-d]pyrimidin-2-yl]-2,6-dimethylphenoxy}acetic acid 98 mg of tert-butyl {4-[5-(trans-2-fluorocyclohexyloxy)-7-propoxyoxazolo[5,4-d]pyrimidin-2-yl]-2,6-dimethylphenoxy}acetate were dissolved in 3.5 ml of dichloromethane, and treated with 1.5 ml of trifluoroacetic acid. After 16 h, the mixture was concentrated and freeze-dried. This gave 96 mg of the title compound.
LC/MS (Method LC1): Rt=1.35 min; m/z=474.20 [M+H]$^+$

(c) tert-Butyl(S)-1-(2-{4-[5-(trans-2-fluorocyclohexyloxy)-7-propoxyoxazolo[5,4-d]pyrimidin-2-yl]-2,6-dimethylphenoxy}acetyl)pyrrolidine-2-carboxylate 82 mg of {4-[5-(trans-2-fluorocyclohexyloxy)-7-propoxyoxazolo[5,4-d]pyrimidin-2-yl]-2,6-dimethylphenoxy}acetic acid were added to 1.5 ml of N,N-dimethylformamide, and 48 mg of 1-ethyl-3-(3-dimethylaminopropyl)carbodiimide hydrochloride, 10 mg of 1-hydroxy-7-azabenzotriazole and 195 µl of N,N-diisopropylethylamine were added, and after 5 min 24 mg of tert-butyl L-prolinate were added. After 16 h at room temperature, 10 ml of water were added, after which the mixture was adjusted to pH 3 by addition of 2 M aqueous hydrochloric acid and extracted twice with ethyl acetate. The combined organic layers were washed with saturated sodium bicarbonate solution and sodium chloride solution, dried and concentrated under reduced pressure. This gave 79 mg of the title compound.
LC/MS (Method LC1): Rt=1.44 min; m/z=627.31 [M+H]$^+$

(d) (S)-1-(2-{4-[5-(trans-2-fluorocyclohexyloxy)-7-propoxyoxazolo[5,4-d]pyrimidin-2-yl]-2,6-dimethylphenoxy}acetyl)pyrrolidine-2-carboxylic acid 76 mg of tert-butyl(S)-1-(2-{4-[5-(trans-2-fluorocyclohexyloxy)-7-propoxyoxazolo[5,4-d]pyrimidin-2-yl]-2,6-dimethylphenoxy}acetyl)pyrrolidine-2-carboxylate were dissolved in 1.6 ml of dichloromethane and 0.8 ml of trifluoroacetic acid. After 16 h at room temperature, the mixture was concentrated under reduced pressure and freeze-dried. This gave 83 mg of the title compound.
LC/MS (Method LC1): Rt=1.33 min; m/z=571.25 [M+H]$^+$ The exemplary compounds of the formula I listed in Table 1 were prepared analogously to the preparation of the exemplary compounds described above. Some of them were obtained in the form of their trifluoroacetate salt.

TABLE 1

Exemplary compounds of the formula I

| Example | Name | LC/MS | m/z [M + H]+ | Rt [min] |
|---|---|---|---|---|
| 3 | (S)-1-(2-{4-[5-(2-Fluorophenoxy)-7-propoxyoxazolo[5,4-d]pyrimidin-2-yl]-2,6-dimethylphenoxy}acetyl)pyrrolidine-2-carboxylic acid | LC1 | 565.38 | 1.32 |
| 4 | (S)-1-(2-{4-[5-(5-Fluoro-2-methylphenoxy)-7-propoxyoxazolo[5,4-d]pyrimidin-2-yl]-2,6-dimethylphenoxy}acetyl)pyrrolidine-2-carboxylic acid | LC1 | 579.40 | 1.36 |
| 5 | (S)-1-(2-{4-[5-(3-Fluoro-4-methylphenoxy)-7-propoxyoxazolo[5,4-d]pyrimidin-2-yl]-2,6-dimethylphenoxy}acetyl)pyrrolidine-2-carboxylic acid | LC1 | 579.42 | 1.36 |
| 6 | (S)-1-(2-{2,6-Dimethyl-4-[7-propoxy-5-(pyridin-3-yloxy)oxazolo[5,4-d]pyrimidin-2-yl]phenoxy}acetyl)pyrrolidine-2-carboxylic acid | LC1 | 546.56 | 1.24 |
| 7 | (S)-1-(2-{4-[5-(2,4-Difluorophenoxy)-7-propoxyoxazolo[5,4-d]pyrimidin-2-yl]-2,6-dimethylphenoxy}acetyl)pyrrolidine-2-carboxylic acid | LC1 | 583.38 | 1.36 |
| 8 | (S)-1-{2-[2,6-Dimethyl-4-(5-phenoxy-7-propoxyoxazolo[5,4-d]pyrimidin-2-yl)phenoxy]acetyl}pyrrolidine-2-carboxylic acid | LC1 | 547.40 | 1.36 |
| 9 | (S)-1-(2-{4-[5-(3-Chlorophenoxy)-7-propoxyoxazolo[5,4-d]pyrimidin-2-yl]-2,6-dimethylphenoxy}acetyl)pyrrolidine-2-carboxylic acid | LC1 | 581.12 | 1.40 |
| 10 | (S)-1-(2-{4-[5-(3-Chlorophenoxy)-7-ethoxyoxazolo[5,4-d]pyrimidin-2-yl]-2,6-dimethylphenoxy}acetyl)pyrrolidine-2-carboxylic acid | LC2 | 567.15 | 1.37 |
| 11 | (S)-1-(2-{4-[7-Ethoxy-5-(3-fluorophenoxy)oxazolo[5,4-d]pyrimidin-2-yl]-2,6-dimethylphenoxy}acetyl)pyrrolidine-2-carboxylic acid | LC2 | 551.15 | 1.33 |
| 12 | (S)-1-(2-{4-[7-Ethoxy-5-(2-fluorophenoxy)oxazolo[5,4-d]pyrimidin-2-yl]-2,6-dimethylphenoxy}acetyl)pyrrolidine-2-carboxylic acid | LC2 | 551.16 | 1.32 |
| 13 | (S)-1-(2-{4-[5-(2,5-Difluorophenoxy)-7-ethoxyoxazolo[5,4-d]pyrimidin-2-yl]-2,6-dimethylphenoxy}acetyl)pyrrolidine-2-carboxylic acid | LC2 | 569.16 | 1.33 |
| 14 | (S)-1-(2-{4-[7-Ethoxy-5-(5-fluoro-2-methylphenoxy)oxazolo[5,4-d]pyrimidin-2-yl]-2,6-dimethylphenoxy}acetyl)pyrrolidine-2-carboxylic acid | LC1 | 565.26 | 1.23 |
| 15 | (S)-1-[2-(2,6-Dimethyl-4-{5-[methyl-(3,3,3-trifluoropropyl)amino]-7-propoxyoxazolo[5,4-d]pyrimidin-2-yl}phenoxy)acetyl]pyrrolidine-2-carboxylic acid | LC3 | 580.25 | 0.80 |
| 16 | (S)-1-{2-[4-(5-Cyclobutylmethoxy-7-propoxyoxazolo[5,4-d]pyrimidin-2-yl)-2,6-dimethylphenoxy]acetyl}pyrrolidine-2-carboxylic acid | LC3 | 539.25 | 0.81 |

Determination of the Pharmacological Activity

A) GTP-γ-S Assay Using Human Edg 1 Receptors

In order to determine the Edg 1 receptor activation by the compounds of the invention, a GTP-γ-S ((GTP-γ-S=guanosine 5'-[thio]triphosphate) assay for G-protein coupled receptor binding based on the scintillation proximity assay principle was used, employing a cell membrane preparation from a CHO Flp-In cell line which constitutively overexpresses the human Edg 1 receptor.

(a) Cell Line Generation

The Flp-In™ expression system (Invitrogen, cat. no. K6010-01) allows the generation of stable mammalian cell lines into which the gene of interest has been integrated through homologous recombination at a specific genomic location called Flp Recombination Target (FRT) site by means of a Flp recombinase encoded by the pOG44 expression plasmid. The integration of the pcDNA5/FRT expression construct into the Flp-In host cell line genome results in the transcription of the gene of interest. The stably transfected cells become hygromycin-resistant.

One day prior to transfection, 200 000 Flp-In-CHO cells were seeded in Ham F-12 medium (Invitrogen, cat. no. 31765) supplemented with 10% fetal calf serum (FCS; Perbio Science, cat. no. SH30068.03) in a 6-well plate and incubated at 37° C./5% $CO_2$ overnight. Using the FuGENE® 6 transfection reagent (Roche, cat. no. 11988387001), cells were cotransfected with the Flp recombinase expression plasmid pOG44 and a modified plasmid additionally containing the edg 1 gene (accession no. NM_001400) termed as pcDNA5-FRT-TO_nFLAG_DEST-EDG 1 with a 9:1 ratio. To obtain the modified pcDNA5-FRT-TO_nFLAG_DEST plasmid, the Invitrogen plasmid pcDNA5/FRT/TO (Invitrogen, cat. no. V6520-20) was adapted to the Gateway® (Invitrogen) cloning system by inserting a Gateway cassette containing attR recombination sites flanking a ccdB gene and a chloramphenicol-resistance gene (Gateway conversion system, Invitrogen, cat. no. 11828-029). In addition a FLAG tag epitope was added before the 5' att recombination site to allow recombinant expression of N-terminally FLAG-tagged proteins.

For the transfection of one well, 1.08 μg of pOG44 and 0.12 μg of pcDNA5-FRT-TO_nFLAG_DEST-EDG 1 were mixed with 100 μl of serum-free Ham F-12 medium containing 6 μl of FuGENE® 6 transfection reagent. After 20 min of incubation, the transfection reagent/DNA complex was distributed dropwise on the cells. The cells were incubated for 24 h at 37° C. Then the cells from 3 wells were transferred to a T75 flask (Greiner Cellstar®, cat. no. 658175) containing Ham F-12 medium supplemented with 10% of FCS but without antibiotic and were incubated for another 24 h. 48 h after transfection, the medium was replaced by selection medium (Ham F-12 supplemented with 10% of FCS and 300 μg/ml of hygromycin B (Invitrogen, cat. no. 10687-010)). The medium was exchanged every 2 to 3 days until a resistant population of cells had grown. Cells were several times splitted and seeded into a new flask so that the cells did not reach more than 25% of confluency. After 2 weeks of selection, the cells were transferred into T175 flasks (Greiner Cellstar®, cat. no. 660175) and cultivated for batch production. Cells were harvested from the culture flasks by short treatment (2 to 5 min) with Accutase (PAA, cat. no. L$^{11}$-007), resuspended in selection medium (see above) and centrifuged at 200×g for 5 min. Cells were resuspended in a mixture of 90% of FCS and 10% of dimethyl sulfoxide and stored frozen in liquid nitrogen.

(b) Membrane Preparation

A membrane preparation was obtained by standard methods from the afore-described CHO Flp-In cell line constitutively overexpressing the human Edg 1 receptor. Briefly, the cryopreserved cells were taken in culture and grown until confluency in T175 cell culture flasks (Becton Dickinson, cat. no. 35 5001). Cell culture was stopped by washing with calcium-free phosphate-buffered saline (PBS; Gibco, cat. no. 14190), and cells were harvested with a rubber-policeman in 4° C. cold and calcium-free PBS supplemented with a protease inhibitor cocktail (complete protease inhibitor; Roche, cat. no. 1697498; 1 tablet per 50 ml) and subsequently centrifuged at 4° C. for 15 min at 1100×g (Heraeus Minifuge T). For cell lysis, the pellet was resuspended in a 4° C. cold hypotonic buffer consisting of 5 mM HEPES (Sigma-Aldrich, cat. no. H-0981), 1 mM EDTA (disodium salt; Merck, cat. No. 8418) supplemented with protease inhibitor cocktail (as above) in which cells were stored for another 15 min on ice. After lysis, cells were centrifuged at 4° C. for 10 min at 400×g (Heraeus Minifuge T). The pellet was disrupted in a Dounce homogenizer, diluted with the supernatant of the previous centrifugation and subsequently centrifuged at 4° C. for 10 min at 500×g (Heraeus Minifuge T) in order to separate nuclei and still intact cells from the membranes mainly present in the supernatant. The supernatant was then diluted in hypotonic buffer and centrifuged (Beckmann, Avanti J251) at approximately 18 600×g for 2 h at 4° C. After centrifugation, the membrane pellet was resuspended in a storing buffer consisting of 20 mM HEPES; 150 mM NaCl (Merck, cat. no. 6400), 1 mM EDTA (as above) supplemented with protease inhibitor cocktail (as above). The membrane preparation was aliquoted and stored at −80 C. Protein concentration of the membrane preparation was determined in a sample by means of a commercial protein assay (Bio-Rad, DC Protein Assay, cat. nos. 500-0113, 500-0114, 500-0115).

(c) GTP-γ-S Assay

The Edg 1 membrane preparation obtained in (b) was employed in a commercially available scintillation proximity assay (SPA) kit for G-protein coupled receptor binding from Amersham Biosciences/GE Healthcare (code RPNQ0210), in which ligand-induced binding of $^{35}$S-radiolabeled GTP-γ-S to the receptor-containing membrane, which is bound to scintillation beads, stimulates the emission of light and allows to quantify the in vitro activity of the Edg 1 agonistic compound. The assay was performed on a 96-well plate substantially according to the manufacturer's instructions. Before start of the experiments, scintillation beads were suspended in a reconstitution buffer consisting of Tris-HCl (pH 7.4) supplemented with 0.1% (w/v) sodium azide and subsequently diluted on ice with assay buffer (consisting of 20 mM HEPES, 100 mM NaCl, 1 mM EDTA (as above), 1 mM dithiothreitol (DTT), adjusted to pH 7.4) to a final bead concentration of 30 mg/ml.

Wells were charged with 10 μl of the specified assay buffer, 10 μl of a 100 μM guanosine diphosphate (GDP) solution, and 10 μl of a solution of the test compound in assay buffer/dimethyl sulfoxide resulting in a final concentration of the test compound of 10 μM. For the high controls, 10 μl of a solution of sphingosine-1-phosphate (S1P; Sigma, cat. no. S-9666), resulting in a final S1P concentration of 10 μM, and for the low controls 10 μl of assay buffer, was added into respective wells instead of the solution of the test compound. All wells contained equivalent amounts of dimethyl sulfoxide. Then 10 μl of a [$^{35}$S]GTP-γ-S solution (4 nM) and the Edg 1 membrane preparation obtained in (b) (15 μg membrane proteins in 100 μl of assay buffer) were added to each well. After incubation of the plates at room temperature for 5 min, 50 μl of the specified scintillation bead suspension (30 mg/ml) was added. After a further incubation period of 45 min at room temperature, plates were centrifuged for 10 min at 500×g. Quantification of [$^{35}$S]GTP-γ-S binding and thus receptor activation was measured by means of a beta counter (MicroBeta, Wallac) over 1 min. Values were background-corrected by subtraction of the respective low control. All measurements were made in triplicate. The receptor activation by the test compound is expressed in percent of the respective high control (10 μM S1P; regarded as 100% activation). In Table 2 activations observed with example compounds at 10 μM are listed.

TABLE 2

Edg 1 receptor activation by example compounds at 10 μM in percent of the activation by 10 μM S1P

| Example | % activation |
|---------|--------------|
| 1 | 101 |
| 2 | 97 |
| 3 | 96 |
| 4 | 110 |
| 5 | 79 |
| 6 | 112 |
| 7 | 90 |
| 8 | 108 |
| 9 | 128 |
| 10 | 69 |
| 11 | 100 |
| 12 | 70 |
| 13 | 95 |
| 14 | 99 |
| 15 | 42 |
| 16 | 85 |

It can be seen from the measurement data that the compounds are highly suitable for wound healing and in particular for treating wound healing disorders of patients with diabetes.

The invention claimed is:

1. A compound of the formula I, in any of its stereoisomeric forms, or a mixture of stereoisomeric forms in any ratio, or a physiologically acceptable salt thereof, or a physiologically acceptable solvate of such a compound or such a salt,

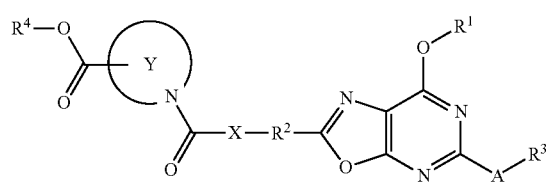

I wherein

A is selected from the group consisting of NH, O and S;

X is selected from the group consisting of $(C_1-C_6)$-alkanediyl, $(C_2-C_6)$-alkenediyl, $(C_2-C_6)$-alkynediyl, $(C_3-C_7)$-cycloalkanediyl and $(C_1-C_6)$-alkanediyloxy, all of which are optionally substituted by one or more identical or different substituents selected from the group consisting of fluorine and hydroxyl, where the oxygen atom of the $(C_1-C_6)$-alkanediyloxy group is attached to the group $R^2$;

Y is a 4-membered to 7-membered saturated or partially unsaturated monocyclic or bicyclic heterocycle which, in addition to the ring nitrogen atom shown in formula I, contains 0, 1, 2 or 3 identical or different ring heteroatoms selected from the group consisting of N, O and S, where one or two of the additional ring nitrogen atoms may carry a hydrogen atom or a $(C_1-C_4)$-alkyl substituent and one of the ring sulfur atoms may carry one or two oxo groups and where the heterocycle is optionally substituted at one or more ring carbon atoms by identical or different $(C_1-C_4)$-alkyl substituents;

$R^1$ is selected from the group consisting of $(C_1-C_6)$-alkyl, $(C_2-C_6)$-alkenyl, $(C_2-C_6)$-alkynyl, $(C_3-C_7)$-cycloalkyl-$C_tH_{2t}$— and Het-$C_tH_{2t}$—, in which t is selected from the group consisting of 0, 1, 2 and 3;

$R^2$ is selected from the group consisting of phenylene and a bivalent radical of an aromatic 5-membered or 6-membered monocyclic heterocycle which contains 1, 2 or 3 identical or different ring heteroatoms selected from the group consisting of N, O and S, where one of the ring nitrogen atoms may carry a hydrogen atom or a substituent $R^{21}$ and where the phenylene and the bivalent radical of an aromatic heterocycle are optionally substituted at one or more ring carbon atoms by identical or different substituents $R^{22}$;

$R^3$ is selected from the group consisting of $(C_1-C_6)$-alkyl, $(C_2-C_6)$-alkenyl, $(C_2-C_6)$-alkynyl, $(C_3-C_7)$-cycloalkyl-$C_uH_{2u}$— and Het-$C_vH_{2v}$—, in which u and v are selected from the group consisting of 1 and 2, or $R^3$ is a radical of a saturated or unsaturated 3-membered to 10-membered monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups and where the radical of a ring is optionally substituted at one or more ring carbon atoms by identical or different substituents $R^{31}$, with the proviso that $R^3$ may not represent $(C_1-C_6)$-alkyl if A represents S;

$R^4$ is selected from the group consisting of hydrogen, $(C_1-C_4)$-alkyl and $(C_3-C_7)$-cycloalkyl-$C_zH_{2z}$—, where z is selected from the group consisting of 0, 1 and 2;

$R^{21}$ is selected from the group consisting of $(C_1-C_4)$-alkyl and $(C_3-C_7)$-cycloalkyl-$C_wH_{2w}$— and oxy, where w is selected from the group consisting of 0, 1 and 2;

$R^{22}$ is selected from the group consisting of halogen, hydroxyl, $(C_1-C_4)$-alkyl-, $(C_1-C_4)$-alkyloxy, $(C_1-C_4)$-alkyl-S(O)$_m$—, amino, nitro, cyano, hydroxycarbonyl, $(C_1-C_4)$-alkyloxycarbonyl, aminocarbonyl and aminosulfonyl;

$R^{31}$ is selected from the group consisting of halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di($(C_1-C_4)$-alkyl)aminosulfonyl;

Het is a radical of a saturated 4-membered to 7-membered monocyclic heterocycle which contains 1 or 2 identical or different ring heteroatoms selected from the group consisting of N, O and S and which is attached via a ring carbon atom, where the radical of a heterocycle is optionally substituted by one or more identical or different substituents selected from the group consisting of fluorine and $(C_1-C_4)$-alkyl;

m is selected from the group consisting of 0, 1 and 2, where all numbers m are independent of one another;

where all cycloalkyl and cycloalkanediyl groups independently of one another and independently of other substituents are optionally substituted by one or more identical or different substituents which are selected from the group consisting of fluorine and $(C_1-C_4)$-alkyl;

where all alkyl, alkanediyl, $C_tH_{2t}$, $C_uH_{2u}$, $C_vH_{2v}$, $C_wH_{2w}$, $C_zH_{2z}$, alkenyl, alkenediyl, alkynyl and alkynediyl groups independently of one another and independently of other substituents are optionally substituted by one or more fluorine substituents.

2. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1, wherein A is selected from the group consisting of O and S.

3. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1, wherein X is selected from the group consisting of $(C_1-C_6)$-alkanediyl, $(C_2-C_6)$-alkenediyl and $(C_1-C_6)$-alkanediyloxy.

4. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1 wherein Y is a 4-membered to 7-membered saturated monocyclic or bicyclic heterocycle which, in addition to the ring nitrogen atom shown in formula I, contains 0 or 1 ring heteroatom selected from the group consisting of N, O and S, where the additional ring nitrogen atom may carry a hydrogen atom or a $(C_1-C_4)$-alkyl substituent and the ring sulfur atom may carry one or two oxo groups and where the heterocycle is optionally substituted at one or more ring carbon atoms by identical or different ($C_1$-$C_4$)-alkyl substituents.

5. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1 wherein $R^1$ is selected from the group consisting of ($C_1$-$C_6$)-alkyl and ($C_3$-$C_7$)-cycloalkyl-$C_tH_{2t}$—, where t is selected from the group consisting of 0, 1 and 2.

6. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1 wherein $R^2$ is selected from the group consisting of phenylene and pyridindiyl, where the phenylene and the pyridinediyl are optionally substituted at one or more ring carbon atoms by identical or different substituents $R^{22}$.

7. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1 wherein $R^3$ is selected from the group consisting of ($C_1$-$C_6$)-alkyl, ($C_3$-$C_7$)-cycloalkyl-$C_uH_{2u}$— and Het-$C_vH_{2v}$—, in which u and v are selected from the group consisting of 1 and 2, or $R^3$ is the radical of a saturated or unsaturated 3-membered to 10-membered monocyclic or bicyclic ring which contains 0, 1 or 2 identical or different ring heteroatoms selected from the group consisting of N, O and S, where one or two of the ring nitrogen atoms may carry a hydrogen atom or a ($C_1$-$C_4$)-alkyl substituent and one of the ring sulfur atoms may carry one or two oxo groups and where the radical of a ring is optionally substituted at one or more ring carbon atoms by identical or different substituents $R^{31}$, with the proviso that $R^3$ may not represent ($C_1$-$C_6$)-alkyl if A represents S;

Het is a radical of a saturated 4-membered to 6-membered monocyclic heterocycle which contains 1 ring heteroatom selected from the group consisting of N, O and S and which is attached via a ring carbon atom, where the radical of a heterocycle is optionally substituted by one or more identical or different substituents selected from the group consisting of fluorine and ($C_1$-$C_4$)-alkyl.

8. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1 wherein A is selected from the group consisting of O and S;

X is selected from the group consisting of ($C_1$-$C_6$)-alkanediyl, ($C_2$-$C_6$)-alkenediyl and ($C_1$-$C_6$)-alkanediyloxy;

Y is a 4-membered to 7-membered saturated monocyclic or bicyclic heterocycle which, in addition to the ring nitrogen atom shown in formula I, contains 0 or 1 ring heteroatom selected from the group consisting of N, O and S, where the additional ring nitrogen atom may carry a hydrogen atom or a ($C_1$-$C_4$)-alkyl substituent and the ring sulfur atom may carry one or two oxo groups and where the heterocycle is optionally substituted at one or more ring carbon atoms by identical or different ($C_1$-$C_4$)-alkyl substituents;

$R^1$ is selected from the group consisting of ($C_1$-$C_6$)-alkyl, ($C_3$-$C_7$)-cycloalkyl-$C_tH_{2t}$— and Het-$C_tH_{2t}$—, where t is selected from the group consisting of 0, 1 and 2;

$R^2$ is selected from the group consisting of phenylene and pyridinediyl, where the phenylene and the pyridinediyl are optionally substituted at one or more ring carbon atoms by identical or different substituents $R^{22}$;

$R^3$ is selected from the group consisting of ($C_1$-$C_6$)-alkyl, ($C_3$-$C_7$)-cycloalkyl-$C_uH_{2u}$— and Het-$C_vH_{2v}$—, in which u and v are selected from the group consisting of 1 and 2, or $R^3$ is a radical of a saturated or unsaturated 3-membered to 10-membered monocyclic or bicyclic ring which contains 0, 1 or 2 identical or different ring heteroatoms selected from the group consisting of N, O and S, where one or two of the ring nitrogen atoms may carry a hydrogen atom or a ($C_1$-$C_4$)-alkyl substituent and one of the ring sulfur atoms may carry one or two oxo groups and where the radical of a ring is optionally substituted at one or more ring carbon atoms by identical or different substituents $R^{31}$, with the proviso that $R^3$ may not represent ($C_1$-$C_6$)-alkyl if A represents S;

Het is a radical of a saturated 4-membered to 6-membered monocyclic heterocycle which contains 1 ring heteroatom selected from the group consisting of N, O and S and which is attached via a ring carbon atom, where the radical of a heterocycle is optionally substituted by one or more identical or different substituents selected from the group consisting of fluorine and ($C_1$-$C_4$)-alkyl.

9. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1 wherein A is O;

X is selected from the group consisting of ($C_1$-$C_6$)-alkanediyl and ($C_1$-$C_6$)-alkanediyloxy;

Y is a 4-membered to 6-membered saturated monocyclic heterocycle which, in addition to the ring nitrogen atom shown in formula I, contains no further ring heteroatoms, where the ring is optionally substituted at one or more ring carbon atoms by identical or different ($C_1$-$C_4$)-alkyl substituents;

$R^1$ is selected from the group consisting of ($C_1$-$C_6$)-alkyl and ($C_3$-$C_7$)-cycloalkyl-$C_tH_{2t}$—, where t is selected from the group consisting of 0 and 1;

$R^2$ is phenylene which is optionally substituted at one or more ring carbon atoms by identical or different substituents $R^{22}$;

$R^3$ is selected from the group consisting of ($C_3$-$C_7$)-cycloalkyl-$C_uH_{2u}$— and Het-$C_vH_{2v}$—, in which u and v are selected from the group consisting of 1 and 2, or $R^3$ is a radical of a saturated or unsaturated 3-membered to 7-membered monocyclic or bicyclic ring which contains 0, 1 or 2 identical or different ring heteroatoms selected from the group consisting of N, O and S, where one or two of the ring nitrogen atoms may carry a hydrogen atom or a ($C_1$-$C_4$)-alkyl substituent and one of the ring sulfur atoms may carry one or two oxo groups and where the radical of a ring is optionally substituted at one or more ring carbon atoms by identical or different substituents $R^{31}$, with the proviso that $R^3$ may not represent ($C_1$-$C_6$)-alkyl if A represents S;

$R^4$ is selected from the group consisting of hydrogen and ($C_1$-$C_4$)-alkyl;

$R^{22}$ is selected from the group consisting of halogen, hydroxyl, ($C_1$-$C_4$)-alkyl and ($C_1$-$C_4$)-alkyloxy;

$R^{31}$ is selected from the group consisting of halogen, ($C_1$-$C_4$)-alkyl, ($C_3$-$C_7$)-cycloalkyl, hydroxyl and ($C_1$-$C_4$)-alkyloxy;

Het is a radical of a saturated 4-membered to 6-membered monocyclic heterocycle which contains 1 ring heteroatom selected from the group consisting of O and S and which is attached via a ring carbon atom, where the radical of a heterocycle is optionally substituted by one or more identical or different substituents selected from the group consisting of fluorine and ($C_1$-$C_4$)-alkyl;

where all cycloalkyl groups independently of one another and independently of other substituents are optionally substituted by one or more identical or different substituents which are selected from the group consisting of fluorine and ($C_1$-$C_4$)-alkyl;

where all alkyl, alkanediyl, $C_tH_{2t}$, $C_uH_{2u}$ and $C_vH_{2v}$ groups independently of one another and independently of other substituents are optionally substituted by one or more fluorine substituents.

10. The compound of the formula I or a physiologically acceptable salt thereof or a physiologically acceptable salvate of such a compound or such a salt as claimed in claim 1, selected from the group consisting of (S)-1-(2-{4-[5-(2,5-difluorophenoxy)-7-propoxyoxazolo[5,4-d]pyrimidin-2-yl]-2,6-dimethylphenoxy}acetyl)pyrrolidine-2-carboxylic acid (S)-1-(2-{4-[5-(trans-2-fluorocyclohexyloxy)-7-propoxyoxazolo[5,4-d]pyrimidin-2-yl]-2,6-dimethylphenoxy}acetyl)pyrrolidine-2-carboxylic acid (S)-1-(2-{4-[5-(2-fluorophenoxy)-7-propoxyoxazolo[5,4-d]pyrimidin-2-yl]-2,6-dimethylphenoxy}acetyl)pyrrolidine-2-carboxylic acid (S)-1-(2-{4-[5-(5-fluoro-2-methylphenoxy)-7-propoxyoxazolo[5,4-d]pyrimidin-2-yl]-2,6-dimethylphenoxy}acetyl)pyrrolidine-2-carboxylic acid (S)-1-(2-{4-[5-(3-fluoro-4-methylphenoxy)-7-propoxyoxazolo[5,4-d]pyrimidin-2-yl]-2,6-dimethylphenoxy}acetyl)pyrrolidine-2-carboxylic acid (S)-1-(2-{2,6-dimethyl-4-[7-propoxy-5-(pyridin-3-yloxy)oxazolo[5,4-d]pyrimidin-2-yl]phenoxy}acetyl)pyrrolidine-2-carboxylic acid (S)-1-(2-{4-[5-(2,4-difluorophenoxy)-7-propoxyoxazolo[5,4-d]pyrimidin-2-yl]-2,6-dimethylphenoxy}acetyl)pyrrolidine-2-carboxylic acid (S)-1-{2-[2,6-dimethyl-4-(5-phenoxy-7-propoxyoxazolo[5,4-d]pyrimidin-2-yl)-phenoxy]acetyl}pyrrolidine-2-carboxylic acid and (S)-1-(2-{4-[5-(3-chlorophenoxy)-7-propoxyoxazolo[5,4-d]pyrimidin-2-yl]-2,6-dimethylphenoxy}acetyl)pyrrolidine-2-carboxylic acid.

11. A pharmaceutical composition, comprising at least one compound of the formula I as claimed in claim 1 or a physiologically acceptable salt thereof, or a physiologically acceptable solvate of such a compound or such a salt, and a pharmaceutically acceptable carrier.

12. A process for preparing a compound of the formula I as claimed in claim 1, wherein a compound of the formula II is reacted with a compound of the formula III,

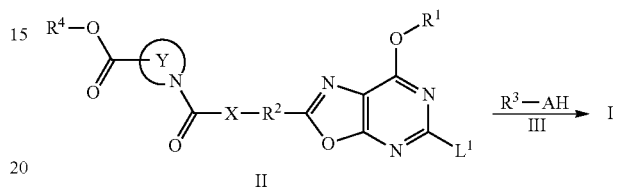

where the groups A, X, Y, $R^1$, $R^2$, $R^3$ and $R^4$ in the compounds of the formulae II and III are defined as in the compounds of the formula I and moreover functional groups may be present in protected form or in the form of a precursor group and the group L' is a halogen atom or a group of the formula —S(O)-Alk or —S(O)$_2$-Alk in which Alk is ($C_1$-$C_4$)-alkyl.

13. A method of treating wound healing disorders in a patient in need thereof comprising administering to said patient a therapeutically effective amount of the pharmaceutical composition of claim 11.

14. A method of wound healing in a patient in need thereof comprising administering to said patient a therapeutically effective amount of the pharmaceutical composition of claim 11.

15. A method of wound healing in diabetics in a patient in need thereof comprising administering to said patient a therapeutically effective amount of the pharmaceutical composition of claim 11.

16. A method of treating diabetic foot syndrome in a patient in need thereof comprising administering to said patient a therapeutically effective amount of the pharmaceutical composition of claim 11.

* * * * *